US008366612B2

(12) United States Patent  
Rosenthal

(10) Patent No.: US 8,366,612 B2  
(45) Date of Patent: Feb. 5, 2013

(54) LARYNGOSCOPE GUIDE AND RELATED METHOD OF USE

(75) Inventor: Jeffrey A. Rosenthal, Grand Rapids, MI (US)

(73) Assignee: Spectrum Health Innovations, LLC, Grand Rapids, MI (US)

(*) Notice: Subject to any disclaimer, the term of this patent is extended or adjusted under 35 U.S.C. 154(b) by 64 days.

(21) Appl. No.: 13/060,483

(22) PCT Filed: Sep. 23, 2010

(86) PCT No.: PCT/US2010/050012
§ 371 (c)(1),
(2), (4) Date: Feb. 24, 2011

(87) PCT Pub. No.: WO2011/038126

PCT Pub. Date: Mar. 31, 2011

(65) Prior Publication Data

US 2011/0201890 A1    Aug. 18, 2011

Related U.S. Application Data

(60) Provisional application No. 61/318,091, filed on Mar. 26, 2010, provisional application No. 61/260,483, filed on Nov. 12, 2009, provisional application No. 61/245,856, filed on Sep. 25, 2009.

(51) Int. Cl.
A61B 1/267 (2006.01)
(52) U.S. Cl. ........................................................ 600/188
(58) Field of Classification Search .................. 600/114, 600/120, 185, 187, 188, 190, 194, 198, 199
See application file for complete search history.

(56) References Cited

U.S. PATENT DOCUMENTS

| 4,865,586 A | 9/1989 | Hedberg |
| 5,235,970 A | 8/1993 | Augustine |
| 5,363,838 A | 11/1994 | George |
| 5,498,231 A | 3/1996 | Franicevic |
| 5,551,946 A | 9/1996 | Bullard |
| 5,645,519 A | 7/1997 | Lee et al. |
| 5,665,052 A | 9/1997 | Bullard |
| 5,810,770 A | 9/1998 | Chin et al. |
| 5,827,178 A | 10/1998 | Berall |
| 5,938,591 A | 8/1999 | Minson |
| 6,146,402 A | 11/2000 | Munoz |

(Continued)

FOREIGN PATENT DOCUMENTS

WO    2009027672    3/2009
WO    2010114867    10/2010

OTHER PUBLICATIONS

International Search Report, International Application No. PCT/US2010/050012, International Filing Date Sep. 23, 2010.

(Continued)

Primary Examiner — Eduardo C Robert
Assistant Examiner — David Comstock
(74) Attorney, Agent, or Firm — Warner Norcross & Judd LLP

(57) ABSTRACT

A method of using a laryngoscope guide including a guiding conduit for advancing an introducer. The method can be used to intubate a subject by positioning the laryngoscope guide in an airway; advancing the introducer in the conduit until an end of the introducer enters the glottis, while viewing images of the introducer end; removing the laryngoscope guide with the guide conduit from the introducer and from the airway; guiding a tube with the introducer until an end of the tube enters the glottis; and removing the introducer from the tube with the end of the tube remaining in the glottis, and in particular, in the trachea, to establish an airway. The guide and method can enable a healthcare professional to intubate a subject where neck mobility is an issue, where an airway is difficult, and/or where a subject is obese.

20 Claims, 15 Drawing Sheets

U.S. PATENT DOCUMENTS

| | | |
|---|---|---|
| 6,569,089 B1 | 5/2003 | Covington et al. |
| 6,652,453 B2 | 11/2003 | Smith et al. |
| 6,655,377 B2 | 12/2003 | Pacey |
| 6,817,973 B2 | 11/2004 | Merril et al. |
| 6,820,614 B2 | 11/2004 | Bonutti |
| D534,652 S | 1/2007 | McGrath |
| 7,320,319 B2 | 1/2008 | Bonutti |
| 7,347,863 B2 | 3/2008 | Rothe et al. |
| 2003/0088156 A1 | 5/2003 | Berci et al. |
| 2003/0195390 A1 | 10/2003 | Graumann |
| 2005/0103333 A1 | 5/2005 | Bonutti |
| 2007/0106121 A1 | 5/2007 | Yokota et al. |
| 2007/0106122 A1 | 5/2007 | Yokota et al. |
| 2007/0106177 A1 | 5/2007 | Yokota |
| 2007/0175482 A1 | 8/2007 | Kimmel et al. |
| 2008/0045801 A1 | 2/2008 | Shalman et al. |
| 2008/0051628 A1 | 2/2008 | Pecherer et al. |
| 2008/0177148 A1 | 7/2008 | Chen et al. |
| 2008/0230056 A1 | 9/2008 | Boedeker |
| 2008/0312507 A1 | 12/2008 | Kim |
| 2009/0216066 A1 | 8/2009 | Bonutti |
| 2009/0299146 A1 | 12/2009 | McGrath |
| 2010/0249513 A1 | 9/2010 | Tydlaska |

OTHER PUBLICATIONS

Written Opinion of the International Searching Authority, International Application No. PCT/US2010/050012, International Filing Date Sep. 23, 2010.

Catanno, David et al., Video Laryngoscopy in Obese Patients, Anesthesiology News Guide to Airway Management, pp. 43-48 (Sep. 2010).

Krage, R. et al., Cormack-Lehane classification revisited, downloaded from http://bja.oxfordjournals.org/cgi/content/abstract/105/2/220 on Aug. 24, 2010.

Verathon reference downloaded from http://www.verathon.com/GS_ProductInformation.htm on Apr. 25, 2010.

Storz, Karl reference downloaded from http://www.epmonthly.com/subspecialties/technology/the-storz-video-laryngoscope/print/ on Apr. 25, 2010.

Pentax reference downloaded from http://ambu.com/COM/Airway_Management/Airway_Management.aspx? GID=GRO . . . on Apr. 25, 2010.

Daiken Medical Co., Ltd reference downloaded from https://www.intubate123.com on Apr. 25, 2010.

McGrath reference downloaded from http://www.aircraftmedical.com/products/series-5 on Sep. 23, 2010.

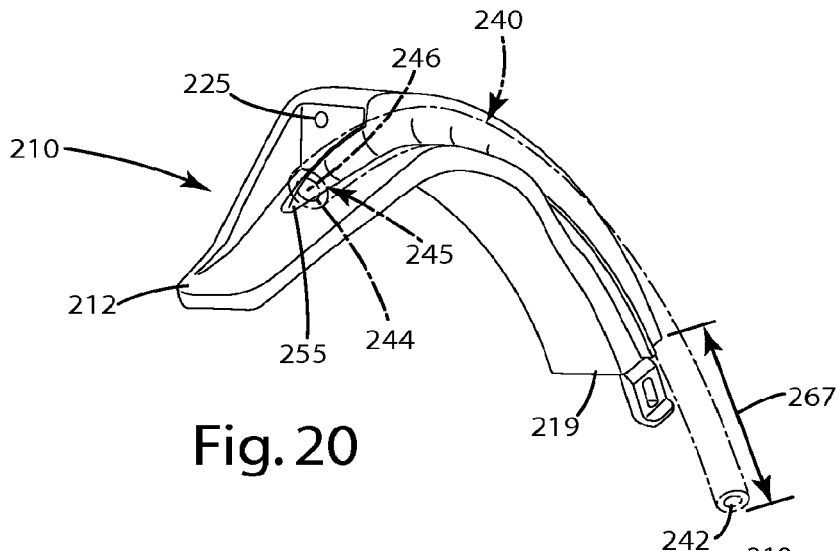
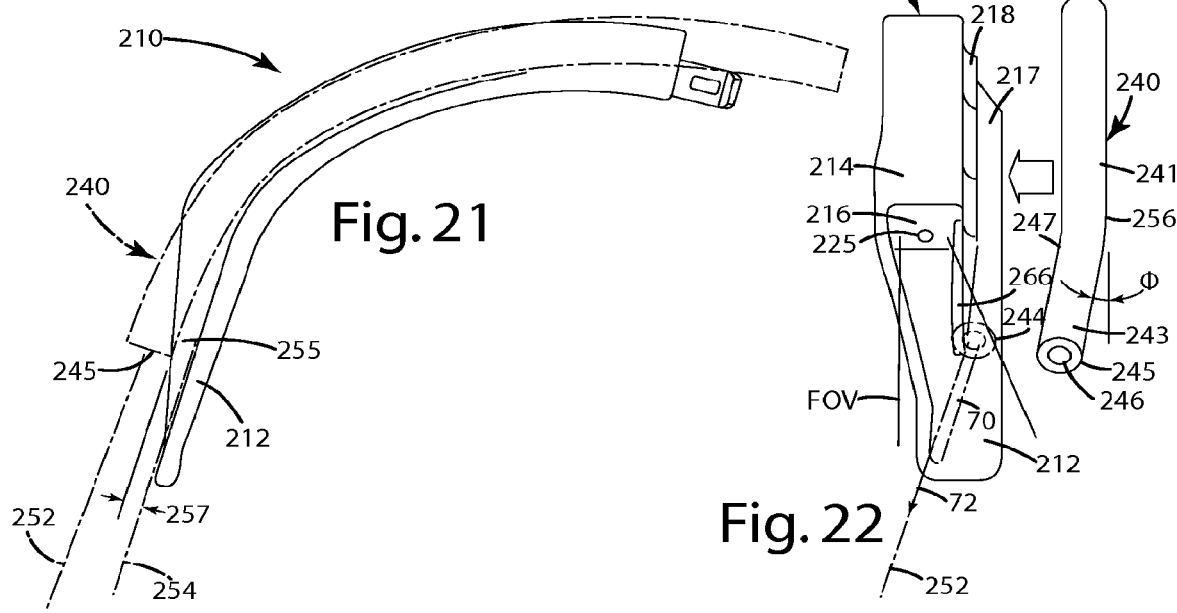
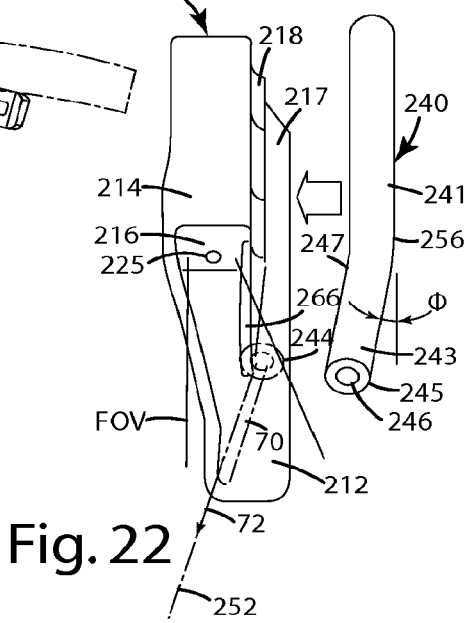
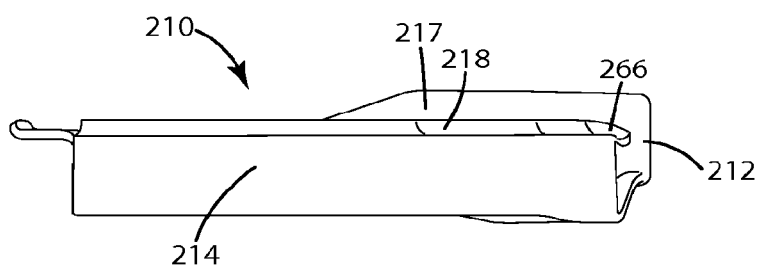
Fig. 20
Fig. 21
Fig. 22
Fig. 23

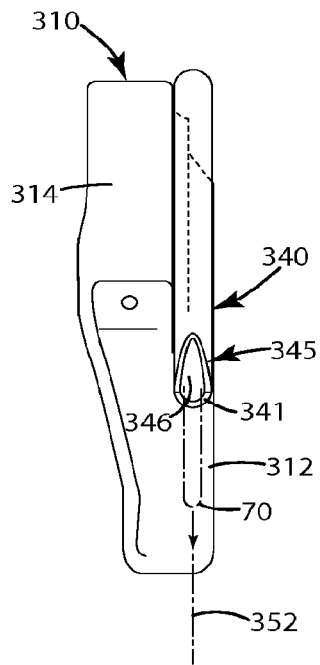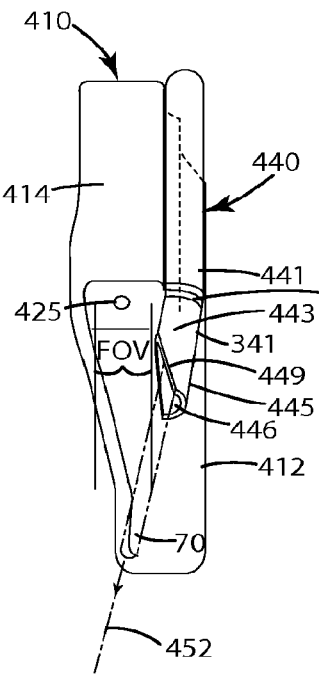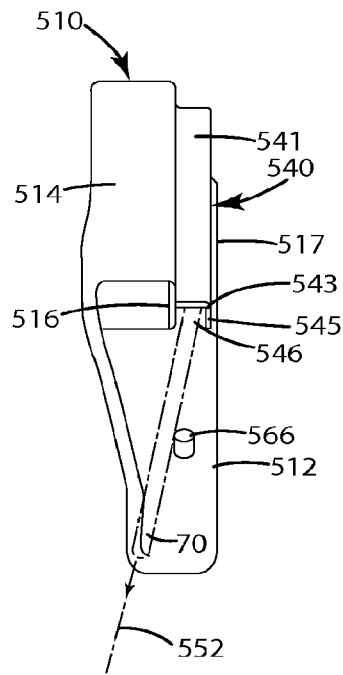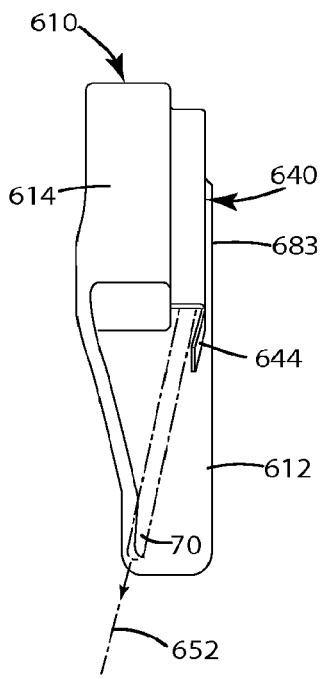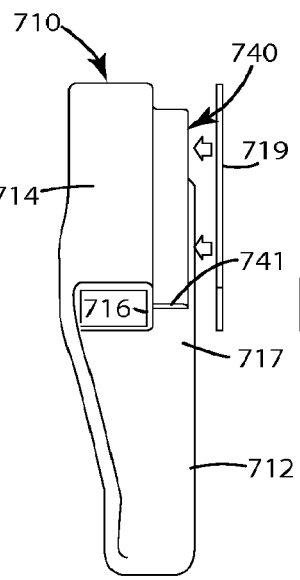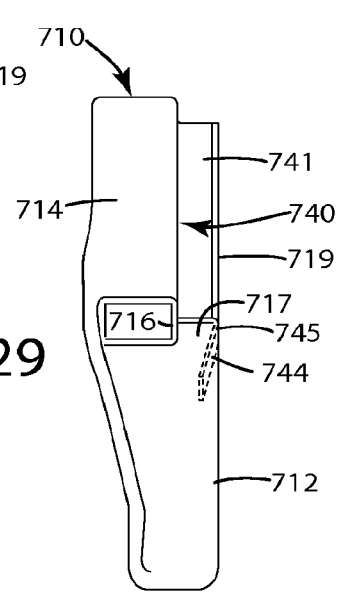

LARYNGOSCOPE GUIDE AND RELATED METHOD OF USE

BACKGROUND OF THE INVENTION

The present invention relates to medical devices, and more particularly, to a laryngoscope guide and related methods of use.

Intubation is a medical procedure used by healthcare professionals to place an endotracheal tube in the trachea of a subject to facilitate breathing, or to permit controlled introduction of gases, such as oxygen or anesthetic gases, through the tube into the subject's airway. This medical procedure has evolved substantially over the years.

An early but still accepted and used intubation procedure is a direct viewing method, in which a professional tilts a subject's head posteriorly, with the subject's neck extended, and peers through the oral cavity, generally down the throat toward the trachea. To assist in viewing, a laryngoscope including a simple handle attached to a blade, is inserted in the mouth with the blade trapping and moving the subject's tongue and/or epiglottis out of the line of sight. This method generally requires that the professional align the oral axis, that is, the axis extending generally into the subject's mouth, with the laryngeal and pharyngeal axes, that is, the longitudinal axes generally corresponding to the subject's larynx and pharynx, respectively. In some cases, the professional also inserts a long, thin stylet or Bougie, independently of the laryngoscope, into the mouth and down through the vocal chords and into the trachea, all while directly viewing the advancement. With the stylet placed, the professional places a larger endotracheal tube over the stylet, and guides it with the Bougie to the trachea to establish an airway. The Bougie is then carefully removed.

Although this method serves its purpose, it can be difficult if not impossible to use on subjects who have abnormal airways, are obese, have undergone trauma requiring a cervical spine collar, have arthritis, have mandibular fractures, have had previous cervical fusion, or are combative. Examples of various stylet laryngoscopy procedures are disclosed in U.S. Pat. No. 4,865,586 to Hedberg, U.S. Pat. No. 5,235,970 to Augustine, as well as U.S. Pat. No. 6,820,614 and U.S. Pat. No. 7,320,319 to Bonutti; and U.S. Patent Publication 2008/0230056 to Boedeker.

Over time, laryngoscopy has implemented viewing devices to obtain an indirect view of the glottis to facilitate intubation. For example, with the advent of fiberoptics, laryngoscopes began to include, and many still do, fiberoptic bundles near the blade that enable a professional to view the subject's anatomy near the blade. Joined with the blade of such devices is a stylet located inside an endotracheal tube, also joined with the blade. In use, the stylet is viewed with the fiberoptics, inserted in the trachea, and the endotracheal tube is placed in the trachea. With the endotracheal tube in place, the laryngoscope blade, fiberoptics, light source and stylet are all simultaneously withdrawn, leaving the endotracheal tube and a related cuff in the airway. Although these devices also serve a purpose, one issue is that the blade, fiberoptics, light source, stylet and endotracheal are all located in the subject simultaneously, which can prove problematic, particularly where the airway is restricted, where the airway has already experienced trauma, or where the subject is obese. Examples of various fiberoptic laryngoscopes are the Bullard Scope disclosed in U.S. Pat. Nos. 5,551,946 and 5,665,052 to Bullard, as well as the laryngoscope disclosed in U.S. Pat. No. 6,146,402 to Munoz.

More recently, laryngoscopes have evolved to include a camera located adjacent the laryngoscope blade that feeds video or images to a viewing monitor attached to a handle of the laryngoscope. The image displayed on the monitor can be viewed by the professional during insertion of the endotracheal tube to assist in guiding the tube into the trachea. Examples of video laryngoscopes are the McGrath® video laryngoscope, available from Aircraft Medical Limited of Edinburgh, Great Britain, the GlideScope®, available from Verathon® Medical of Bothell, Wash., the Pentax AWS, available from Pentax Medical Company of Montvale, N.J., the Storz C-Mac, available from Karl Storz GmbH of Tuttlingen, Germany, and the Daiken Medical Coopdech C-Scope, available from Daiken Medical Co., Ltd of Osaka, Japan. Further examples of more recent viewing devices including laryngoscopes are disclosed in U.S. Pat. No. 5,827,178 to Berall; U.S. Pat. No. 6,652,453 to Smith; and U.S. Patent Publications 2003/0195390 to Graumann; 2007/0175482 to Kimmel; 2008/0177148 to Chen; 2008/0051628 to Pecherer and 2008/0312507 to Kim, A potential issue with many video laryngoscopes is that they are designed to operate as a physically separate component from the endotracheal tube. For example, the blade of most standard video laryngoscopes is inserted first into the mouth and positioned to image the vocal chords and trachea so the professional can view these features on a viewing screen. Next, the endotracheal tube is placed in the mouth and forced toward the vocal chord opening, with the end of the tube eventually coming into view of the camera of the device. In such a procedure, the professional must blindly steer the tube from a point where they lose view of the tube in the mouth to the point where the end of the tube is picked up by the camera. In some cases, while being blindly steered, the tube may steer in the wrong direction, may get hung up on tissue (particularly in obese subjects), or may unintentionally abrade or agitate tissue in the region where it is blindly steered.

Further, even after the end of the endotracheal tube comes into view of the camera so it can be viewed by the professional on the screen, the tube can be difficult, and in some cases impossible, to steer into the trachea, particularly in subjects having difficult anatomy, where the professional is inexperienced or where the professional is rushed to get an airway established due to the condition of the subject. Some video laryngoscope manufacturers have attempted to address this inherent steering deficiency by providing a rigid, preformed rod over which the endotracheal tube is positioned before the tube is inserted in the airway, independently of the laryngoscope blade. The rigid rod can provide some degree of steering to the tube, which otherwise might be flexible. Even with the rigid rod in the tube, however, directing the endotracheal tube can be challenging and time consuming—which is usually unacceptable when every second counts in establishing an airway.

Other video laryngoscope manufacturers have attempted to develop a completely different solution to steer the endotracheal tube. For example, certain laryngoscopes have blades including independent and separated retaining clips. Some laryngoscopes have blades including an open groove in a lateral portion of the guide. In these constructions, the endotracheal tube is captured in the clips or the groove, and advanced with the blade into the subject's oral cavity toward the trachea. With the tube attached to the blade, the laryngoscope blade can be used to place the tube by manipulating to the blade. Of course, if the end of the endotracheal tube is to be moved substantially laterally, the blade likewise will be moved substantially laterally. In some cases, the blade may be restricted from such lateral movement due to a difficult anatomy or immobility of the subject.

Another issue with some laryngoscope guides including clips or grooves is that they can be difficult to use with endotracheal tubes including cuffs disposed at the end of the tubes. For example, the cuffs of many endotracheal tubes are delicate and can tear easily. Therefore, they are not well suited to advance through any type of groove. In addition, the cuff of these types of endotracheal tubes can present a viewing obstacle when they are placed beside or in front of a camera of the device. In some cases the cuff completely obscures the target toward which the endotracheal tube is advanced.

In addition, after a tube is placed with such a construction, the laryngoscope is separated from the endotracheal tube leaving the endotracheal tube in place. The separation of the tube from the blade is usually accomplished by wrenching the endotracheal tube laterally away from the blade. In some cases, this can be difficult, as it requires ample space within the anatomy of the airway to enable the tube to be separated from the blade. Many times, there simply is no such "extra" space. Moreover, in subjects with traumatized or damaged vocal chords or other tissue, this lateral movement of the endotracheal tube can complicate matters. Examples of various laryngoscopes including endotracheal tube retainers are disclosed in WO 2009/027672 (PCT/GB2008/002903) to McGrath and U.S. Patent Publication 2007/0106117 to Yokota.

Despite issues concerning endotracheal tube guidance, video laryngoscopes are becoming an increasingly used tool in performing laryngoscopy, particularly in obese and morbidly obese subject populations. Obese subjects typically have reduced functional residual capacity with decreased pulmonary oxygen stores, leading to rapid desaturation, which means that rapid intubation can be even more desirable in such subjects. Obese subjects also typically have a short neck, a large tongue and redundant folds of oropharyngeal tissue, which can make intubation difficult and can increase the risk of airway obstruction. Cattano, David et. al., *Video Laryngoscopy in Obese Subjects*, Anesthesiology News Guide to Airway Management, pp. 43-48 (September 2010). With video laryngoscopes, healthcare professionals can perform laryngoscopy on obese subjects with reduced risk for airway trauma or damage. Id at 45. However, the amount of time it takes to intubate obese patients with video laryngoscopes is a disputed limitation associated with the video laryngoscopes. Id. at 46.

Although laryngoscopy has evolved over the years, and is making use of current video technology, there still remains long felt and unmet needs to: reduce the amount of time to intubate subjects, for example, in obese subjects and subjects with difficult airways; to decrease potential damage and trauma to the airway; and to intubate in an efficient manner, even in cases where the professional does not have a significant amount of experience in performing the procedure. There also seems to be many attempted solutions to address this need, however, they all seem to fall short, and many seem to be pointing in different directions. For example, as noted above, some position endotracheal tubes separately from the laryngoscope and attempt to use rigid guides to guide the tubes, while others place the endotracheal tubes in grooves or clips of the laryngoscope in an attempt to direct the tube. Thus, it appears that many of the presently attempted solutions teach away from one another.

SUMMARY OF THE INVENTION

A laryngoscope guide including a guiding conduit for advancing an introducer and a related method of use is provided.

In one embodiment, the method of use includes intubating a subject by: positioning the laryngoscope guide in a subject's airway; advancing the introducer in the guiding conduit until an end of the introducer enters the glottis, while viewing images of the to introducer end as it advances; removing the laryngoscope guide with the guide conduit from the introducer and from the airway; sliding a tube relative to the introducer until an end of the tube enters the glottis; and removing the introducer from the tube with the end of the tube remaining in the glottis, and in particular, in the trachea.

In another embodiment, the method of use includes intubating a subject as described in the embodiment above while the subject's head is in a neutral position, with an oral axis of the subject misaligned with both of a pharyngeal axis and a laryngeal axis of the subject. This can enable a healthcare professional to intubate a subject where neck mobility is an issue, where an airway is difficult, where a subject is too obese to offer normal head extension and subsequent intubation, or in other difficult situations.

In yet another embodiment, the method of use includes intubating a subject using a laryngoscope guide which includes a blade and a guide conduit. The laryngoscope guide can be inserted in a subject with the blade displacing tissue, such as the tongue and/or epiglottis of the subject, and to permit visualization of the glottis via an imaging system and monitor joined with the laryngoscope guide. Before, during or after the blade insertion, a guide element, for example, a stylet, rod, or more generically an introducer, can be inserted in an entrance of the guide conduit. With the laryngoscope blade appropriately positioned in the subject, the introducer can be advanced through the guide conduit. An end of the introducer can be inserted into the glottis, while being viewed via the imaging system and monitor. The introducer end can be advanced to the subject's laryngeal entrance and can continue past the vocal chords, and at least partially in or adjacent, and aligned with the trachea to the extent desired. The laryngoscope and guide blade can be removed from the subject with the introducer end remaining in or adjacent the trachea, and with the guide conduit moving, and optionally coaxially sliding, relative to the introducer. An endotracheal tube can be placed over a portion of the introducer and slid down the introducer so that the distal end of the tube reaches or passes the introducer end, until the distal end of the tube is to satisfactorily placed in or adjacent the trachea. With the endotracheal tube end placed in the trachea, the introducer can be removed from the endotracheal tube and removed from the subject.

In still another embodiment, the laryngoscope guide can be joined with an imaging system having a field of view within which an optical axis projects and can include a blade having a distal tip. The guide conduit can terminate at an exit near the distal tip, and can define an advancement axis that projects into the field of view. The advancement axis can be disposed at a first angle relative to the optical axis and oriented to traverse the optical axis. With this construction, the end of the introducer can be easily viewed and optionally steered in the field of view by a healthcare professional.

In still yet another embodiment, the laryngoscope guide can be joined with an imaging system having a field of view and can include a blade having a distal tip and a first blade plane that generally bisects the distal tip and/or the blade. A guide conduit can terminate at an exit near the distal tip, and can define an advancement axis disposed at a first angle relative to the first blade plane so that an introducer projecting along the advancement axis aligns to intersect the first blade plane, optionally laterally entering the field of view of the imaging system. With this construction, the end of the introducer can be easily viewed and optionally steered in the field of view by a healthcare professional.

In a further embodiment, the laryngoscope guide can include a guide conduit for guiding an introducer and a blade that defines a second blade plane that generally extends between opposing lateral portions of the blade. The conduit can be positioned so that an exit of the conduit is located a preselected distance above the second blade plane. An advancement axis of the conduit can be oriented so as to diverge away from the second blade plane. Optionally, as the introducer is advanced along the advancement axis, it diverges away from the second blade plane and aligns with a laryngeal axis of the subject. With this construction, the guide blade can engage tissue of the subject to satisfactorily move it and provide a volume within which to view the glottis, while the guide conduit can precisely project the introducer toward the glottis, generally aligned with the laryngeal axis to facilitate insertion into the trachea.

In yet a further embodiment, the laryngoscope guide conduit can be configured so that the introducer and the guide conduit slide coaxially relative to one another, optionally when advancing the introducer along the advancement axis, and further optionally when removing the laryngoscope guide and conduit from the introducer while leaving a distal end of the introducer in a preselected location, such as within the glottis, trachea, larynx or other opening. With this construction, the introducer can be easily and quickly inserted and readied in the preselected location so that a tube can be guided by the introducer. Further, because the movement of the introducer and guide in such a construction are generally aligned with the oral, laryngeal and/or pharyngeal axes, there is a reduced likelihood that the laryngoscope guide and its components will traumatize or otherwise disturb tissue when it is removed from the introducer.

In still yet a further embodiment, the guide conduit can be positioned within the lateral dimensions of the tip or other portions of the blade so that it does not interfere with insertion of the laryngoscope guide blade and/or contact the tongue and/or vocal chords of the subject.

In another further embodiment, the guide conduit can be a tubular conduit defining an entrance and an exit. The exit can be located at or near the distal tip of the laryngoscope blade, while the entrance can be located distal from the tip, for example, near the attachment end of the laryngoscope guide, or near the handle of the laryngoscope. Optionally, the exit can be forward of the imaging system so that the introducer is placed in close proximity to the preselected location.

In yet another further embodiment, the guide conduit can be fully enclosed along at least a portion of its length. Optionally, the guide conduit can be adapted to fully circumferentiate or surround a guide element positioned in that portion of the guide conduit. Further optionally, the introducer can be constrained by the guide conduits so that it is not laterally removable from the conduit in use.

The laryngoscope guide and related methods of use herein provide a simple and efficient way to treat subjects. Where the laryngoscope guide includes a guide conduit, a healthcare professional can quickly advance an introducer and precisely steer the distal end of the introducer toward a preselected location, such as a glottis, trachea, larynx or other opening. Where the conduit provides an advancement axis that is aligned to intersect a blade or tip bisecting plane, midline or an optical axis, the distal tip of the introducer can be clearly viewed in a field of view of an imaging system, which can further assist the healthcare professional in quickly placing the distal tip of the introducer in the preselected location.

Where the laryngoscope guide with guide conduit are used to place the introducer, an endotracheal or other tube can be quickly moved relative to the introducer, using the introducer as a guide for the tube, and inserted in a preselected location to provide the desired treatment to the subject. Although this is a significant divergence from current trends in the art to advance a complete endotracheal tube in grooves or clips of a laryngoscope blade, or to advance the tube physically independently of the laryngoscope guide altogether, it yields surprising and unexpected results. For example, instead of the steps of: inserting the introducer in the preselected location using the guide; removing the laryngoscope guide; and guiding the tube with the introducer, slowing down time to intubation—these are, after all, extra steps—the methods and devices herein speed up time to intubation, apparently due to enhanced viewing and steering of the introducer to efficiently insert the introducer in the preselected location. Moreover, with the ease of use and maneuverability of the laryngoscope guide described herein, less experienced healthcare professionals can improve time to intubation, and a wider variety of subjects can be quickly and efficiently intubated, including obese subjects, subjects with difficult airways, and even subjects that can only be intubated when in a neutral head position. Accordingly, the methods and devices herein also satisfy long felt needs.

These and other objects, advantages and features of the invention will be more readily understood and appreciated by reference to the detailed description of the invention and the drawings.

BRIEF DESCRIPTION OF THE DRAWINGS

FIG. 20 is a front perspective view of a fifth alternative embodiment of the laryngoscope guide;

FIG. 21 is a side view of the fifth alternative embodiment of the laryngoscope guide;

FIG. 22 is a front view of the fifth alternative embodiment of the laryngoscope guide before joining of a guide conduit;

FIG. 23 is a rear view of the fifth alternative embodiment of the laryngoscope guide that does not include a guide conduit;

FIG. 24 is a front view of a sixth alternative embodiment of the laryngoscope guide;

FIG. 25 is a front view of a seventh alternative embodiment of the laryngoscope guide;

FIG. 26 is a front view of a eighth alternative embodiment of the laryngoscope guide;

FIG. 27 is a front view of a ninth alternative embodiment of the laryngoscope guide;

FIG. 28 is a front view of a tenth alternative embodiment of the laryngoscope guide before a guide conduit plate is joined with the laryngoscope guide;

FIG. 29 is a perspective view of the guide conduit plate of the tenth alternative embodiment of the laryngoscope guide;

FIG. 30 is a front view of the tenth alternative embodiment of the laryngoscope guide having a guide conduit plate joined with the laryngoscope guide;

DETAILED DESCRIPTION OF THE CURRENT EMBODIMENTS

I. Construction

Figure 1:
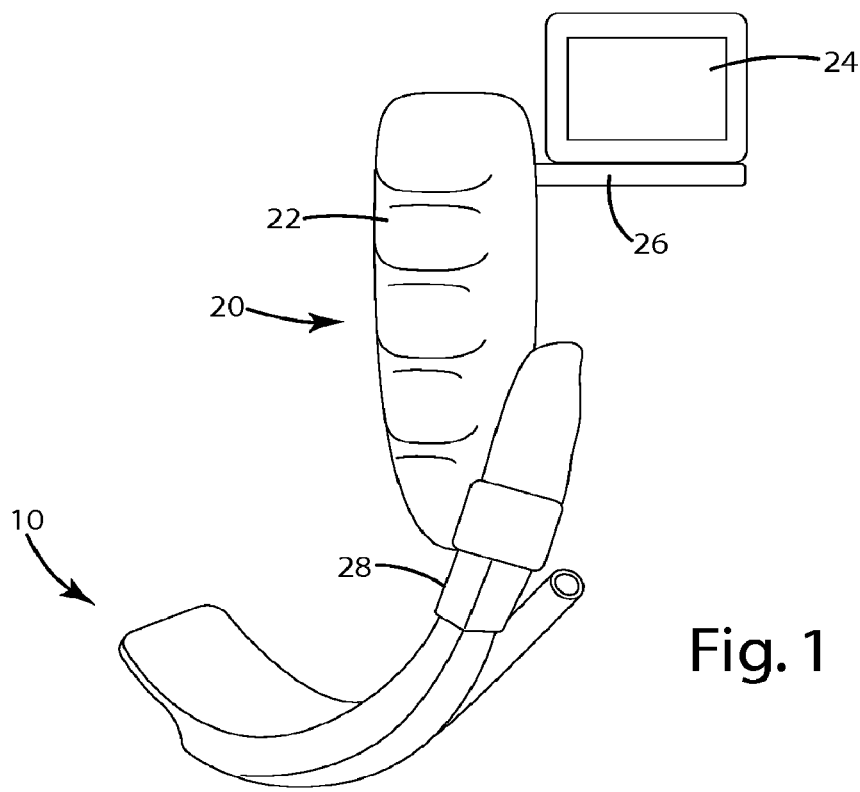
FIG. 1 is a perspective view of a laryngoscope guide of a current embodiment joined with a laryngoscope.

A current embodiment of the laryngoscope guide is illustrated in FIGS. 1-7 and 12 and generally designated 10. As shown in FIG. 1, the laryngoscope guide 10 can be joined with a laryngoscope 20. The laryngoscope can include an elongated handle 22 which can be ergonomically shaped to be gripped by a healthcare professional and easily manipulated while the professional is performing a laryngoscopy. The laryngoscope can include a viewing element 24, which can be a monitor or a video screen that is mounted to the handle 22 via an arm 26. As illustrated, the monitor 24 can joined directly with the handle 22 and generally can be adapted to move with the handle or other components of the laryngoscope as the professional manipulates it. The laryngoscope can include a laryngoscope blade attachment portion 28 where the laryngoscope guide 10 is joined with a fastening mechanism to the handle.

One exemplary laryngoscope suitable for use with the laryngoscope guide is the McGrath® Series 5 video laryngoscope, which is commercially available from Aircraft Medical Limited of Edinburgh, United Kingdom. This video laryngoscope is described in PCT Application No. PCT/GB2008/002903, which is hereby incorporated by reference. A generally unmodified, guide suitable for use with the McGrath® Series 5 video laryngoscope is shown in U.S. Pat. No. D534,652 to McGrath, which is also hereby incorporated by reference herein. Other exemplary laryngoscopes suitable for use with the laryngoscope guide herein are the GlideScope®, available from Verathon® Medical of Bothell, Wash., the Pentax AWS, available from Pentax Medical Company of Montvale, N.J., the Storz C-Mac, available from Karl Storz GmbH of Tuttlingen, Germany, and the Daiken Medical Coopdech C-Scope, available from Daiken Medical Co., Ltd of Osaka, Japan.

The laryngoscope guide 10 of the current embodiment is illustrated as a detachable, removable and disposable laryngoscope guide, however, the laryngoscope guide 10 can form an integral, non-removable portion of a laryngoscope construction. For example, the components of the guide 10 described herein can be permanently incorporated into a laryngoscope blade of a laryngoscope. The components can be constructed from materials such as stainless steel, metal, or other sterilizable or autoclavable materials to provide multiple uses without spreading pathogens among subjects. Moreover, if desired, the laryngoscope guide 10 can be used with a non-portable, non-handheld video laryngoscope having a separate viewing monitor which can be viewed by the professional and/or multiple observers simultaneously. The separate viewing monitor can be connected to the handle or imaging system via wires, or the laryngoscope 20 can be outfitted with a transmitter or receiver to communicate image data wirelessly to a physically separate monitor (not shown). If desired, in either construction where the monitor is separate or directly joined with the handle, the laryngoscope can be wirelessly capable of communicating the image data captured by the imaging system 25 to yet another monitor or computer (not shown) to enable the image data to be separately viewed, stored or processed for the particular procedure with which the device is used.

Figure 2:
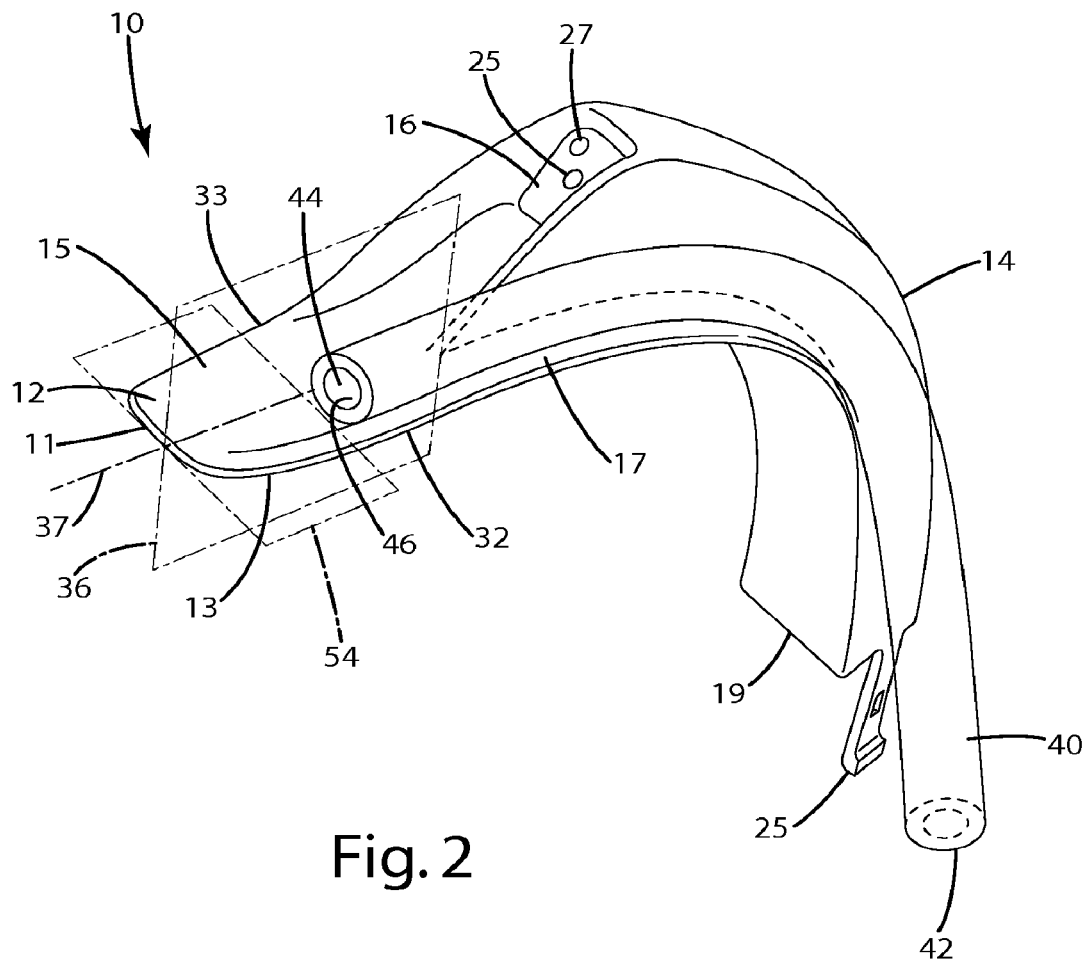
FIG. 2 is a perspective view of the laryngoscope guide.
Figure 3:
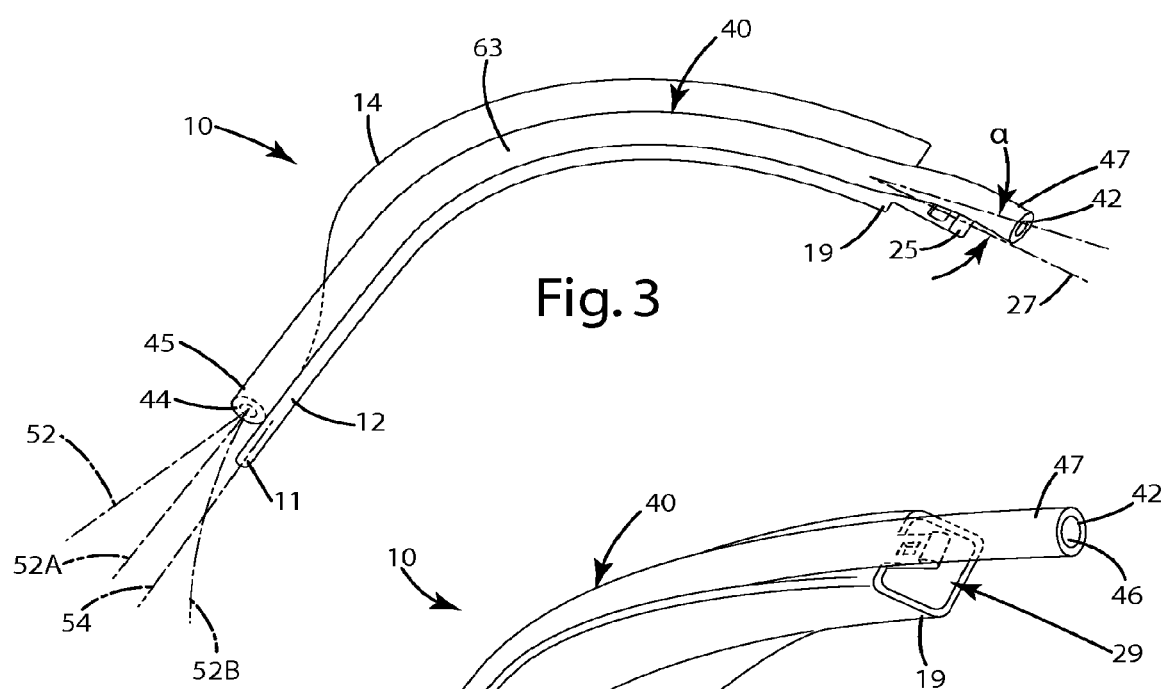
FIG. 3 is a side view of the laryngoscope guide.
Figure 4:
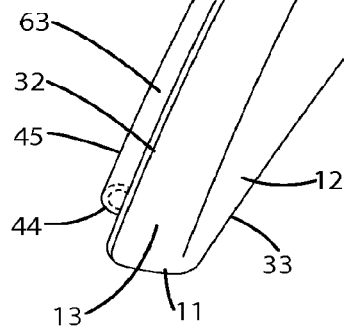
FIG. 4 is another perspective view of the laryngoscope guide.
Figure 7:
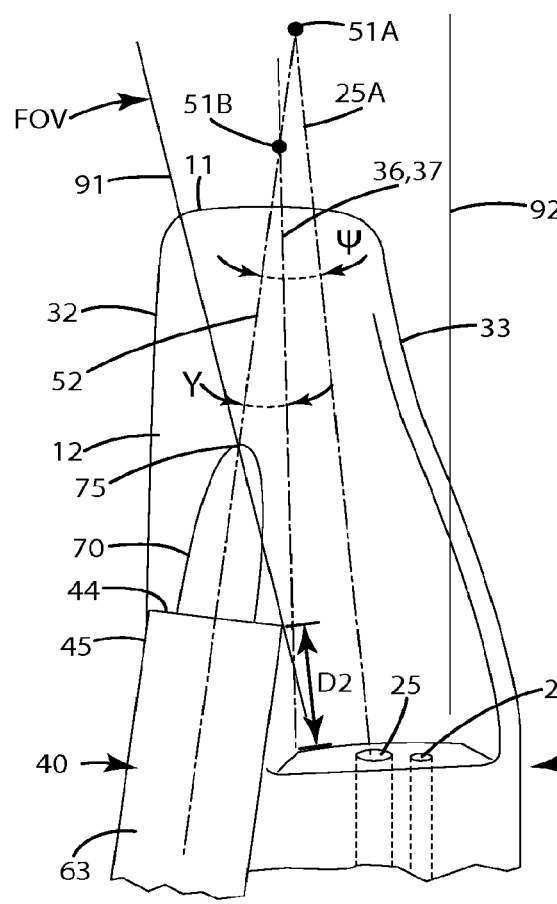
FIG. 7 is a top view of the laryngoscope guide of the current embodiment illustrating orientation of certain axes and planes.

In the current embodiment as shown in FIGS. 1-5, the imaging system 25 can communicate images or video to the monitor 24. The laryngoscope guide 10 can include an imaging portion 14 joined with a blade 12. The imaging portion 14 can house components of the imaging system 25 that enable a professional to view the advancement of the blade 12 in the subject, for example toward the glottis and trachea, using the laryngoscope 20. As a further example, the imaging portion 14 can define a bore 29 within which a portion of the imaging system 25 and/or light source 27 extends, as shown in FIGS. 4 and 7. The imaging portion 14 can include a viewing window or other transparent or translucent section 16 through which a light source 27 and image collecting components of the imaging system 25 can emit light or collect image data, respectively. These image collecting components can sense and collect image data to the monitor 24, and optionally can be any video or digital camera, CMOS array, CCD array, or other component of the imaging system 25 able to capture images. Optionally, in some cases, the viewing window 16 can be a simple opening defined in the imaging portion of the laryngoscope guide, rather than a transparent window or lens in the guide. In such a construction, the imaging system 25 and its components might be subjected to fluids during use, and therefore might be configured to be easily sterilized or otherwise cleaned. Further optionally, the viewing window 16 can be outfitted with lenses or other optical features to supplement the imaging system 25.

Figure 5:
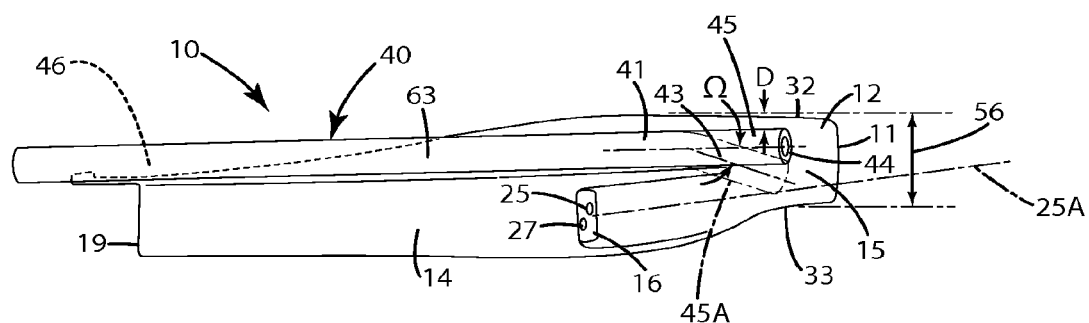
FIG. 5 is a top view of the laryngoscope guide.
Figure 6:
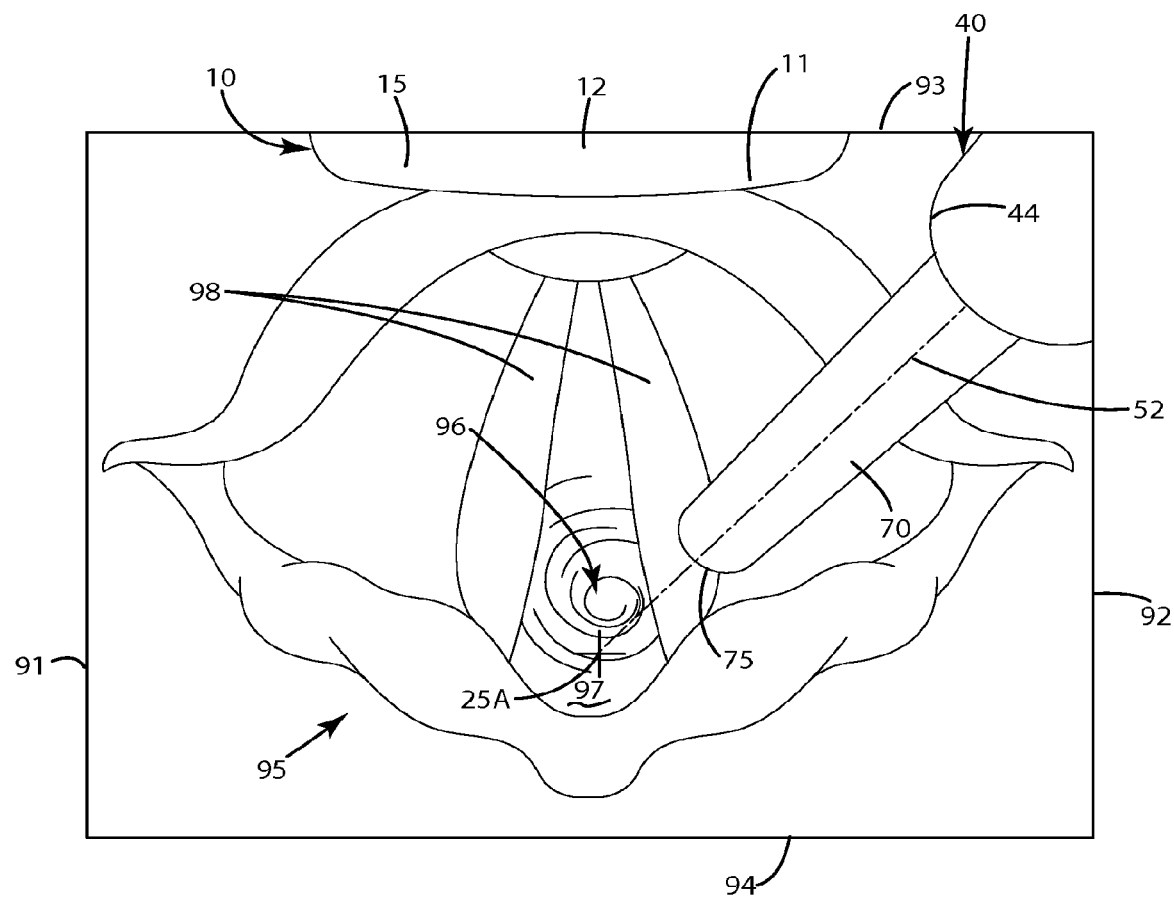
FIG. 6 is a view of a field of view of an imaging system of the laryngoscope.

With reference to FIGS. 5-7, the imaging system 25 can have a field of view FOV within which an optical axis 25A projects. Although referred to as an optical axis, this axis 25A can be associated with components, such as arrays and sensors that are not truly optical in nature, In general, the optical axis refers to a line generally formed by the principal axis or axes of one or more sensing elements or lenses. Depending on the orientation of the imaging system and the inclusion of any optional lenses in the guide or the system, the optical axis can project along a variety of different directions relative to the guide 10 and various reference axes of the guide 10 and its components as described below. A few examples of suitable imaging system components include those disclosed in U.S. Patent Publications 2009/0299146 to McGrath and 2007/0106117 to Yokota which are incorporated by reference herein. Of course, other imaging systems can be used as well.

The field of view FOV of the imaging system 25 can be dictated by the imaging components of the imaging system and/or lenses built in to the guide 10. As illustrated in FIGS. 6-7, the field of view FOV can include a first lateral portion 91, a second lateral portion 92, an upper portion 93 and a lower portion 94. Of course, although shown in a generally rectangular format, the field of view FOV could also be presented in a circular, elliptical or other geometric presentation, with the above portions still being applicable to reference the parts of the field of view. Further, the field of view of the imaging system can be designed so that it can capture a sufficient portion of the preselected location to be viewed within an airway or other internal space of the subject to perform a desired procedure. For example, the imaging system can be configured so that the field of view FOV encompasses and provides a professional with a complete view on a monitor of a preselected location when performing an intubation on a subject. Such a preselected location, as used herein, can include the glottis 95, trachea 96, larynx, and/or the opening 97 between the vocal folds 98 that leads to the trachea 96, which are illustrated in FIG. 6.

The laryngoscope blade 12 can form a portion of the laryngoscope guide, and where included can be joined with and extend forwardly of and beyond the imaging system 25 and/or the imaging portion 14. The blade 12 can include an inferior portion 13 and a superior portion 15. The imaging element portion 14 can be located adjacent the superior portion 15, with the superior portion laying at least partially in or at least slightly below the field of view FOV. The blade 12 can transition to or otherwise include a flange 17 that projects laterally adjacent the imaging element portion 14. This flange can extend generally from the distal tip 11 of the blade 12 toward the attachment end 19 of the laryngoscope guide 10.

The blade 12 can include a lateral portion 32 and a medial portion 33, generally referred to as opposing lateral portions at which the respective superior and inferior portions can terminate. The distal tip 11 of the blade can also extend between these lateral 32 and medial 33 portions. In so doing, the distal tip can generally extend in a linear fashion, so that the end of the blade is somewhat squarish with rounded corners. Of course, in certain applications, the distal tip can be more rounded, and generally in the form of a semicircle between the lateral and medial portions. Further, if desired, the distal tip can include a pointed or angular end, depending on the application and intended use. The lateral and medial portions can generally form the outermost lateral dimensions 56 of the blade (FIG. 5), as described below.

As shown in FIGS. 2 and 7, the blade 12 can define a first blade plane 36 that is located about midway between the lateral 32 and medial 33 portions of the blade. This first blade plane 36 can generally intersect the blade 12 at a midline or middle axis 37, and as shown in FIG. 2, can extend generally vertically relative to the blade 12, and more particularly to the superior portion 15 of the blade 12, regardless of whether that superior portion is planar or curved. The first blade plane 36 can generally bisect the blade 12 and/or the distal tip 11, and form a reference plane to establish spatial relationships between different components and axes of those components as described further below. Optionally, the midline or middle axis 37 can be independent of any plane, such as the first blade plane 36, and can simply be a line located on the distal tip 11 midway between the lateral and medial portions 32, 34 of the blade.

Figure 12:
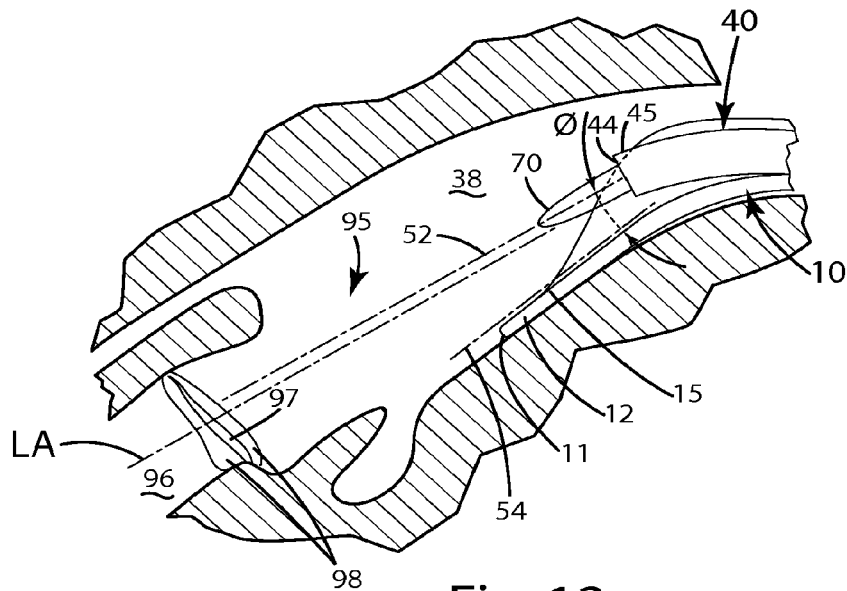
FIG. 12 is a sectional view of the laryngoscope guide of the current embodiment oriented to align an advancement axis with the laryngeal axis of the subject.

As shown in FIGS. 2, 3 and 7, the blade 12 can define a second blade plane 54. This second blade plane 54 can be generally perpendicular to the first blade plane, and can extend generally between the lateral and medial portions 32, 33 of the blade, or more generally across the blade and/or distal tip 11 of the blade. As shown in FIG. 12, the second blade plane can begin at the exit end 45 of the conduit, generally under the exit 44 and extend along or through at least a portion of the superior portion 15 of the blade 12, optionally extending toward and beyond the distal tip 11 of the blade. Optionally, the blade 12 and/or superior portion 15 may not be as linear or planar as those shown in FIG. 12. For example, the blade and/or superior portion may continue from below the conduit 40 toward the distal tip 11 as an arc-shape, or as a shape having a curve, or as a shape having one or more compound curved planes. In such a construction having an arc-shape or curvilinear surface, the second blade plane 54 can be defined by the plane that is tangent to the superior portion 15 of the blade immediately under the exit 44 of the conduit 40.

The blade 12 can be of sufficient strength and configured to engage a subject's anatomy while intubating the subject. For example, as shown in FIGS. 12-19, the blade can be of sufficient strength and rigidity so that when a professional presses the inferior portion 13 against the subjects tongue, epiglottis, or more generally mandibular structures, to establish a viewing volume 38 (FIGS. 12-13) within the subject's airway, the blade will not significantly deflect, deform or break unintentionally. In some cases, the professional can exert a force of between 1 to 15 pounds in moving the subjects tissue to establish a viewing volume. The force exerted can be greater for obese and morbidly obese subjects.

Where the guide 10 is adapted to be disposable, as shown in FIGS. 2 and 4, the guide 10 can include an attachment end 19 having one or more fastening elements 25 to join the laryngoscope guide 10 with the laryngoscope 20 in removable fashion so that the laryngoscope guide 10 can be detached from the laryngoscope 20 and disposed of appropriately. Although shown as a tab-like fastener, the attachment fastener 25 can be modified to any conventional alternative construction appropriate for the application. Of course, where the laryngoscope guide forms an integral part of the laryngoscope, the fastener can be of a more permanent construction, and in some cases, can be eliminated all together with the laryngoscope guide being joined integrally with the laryngoscope 20.

Returning to FIGS. 2-7, the laryngoscope guide 10 can include a guide element, also referred to as a guide conduit 40. Generally, the guide conduit can be configured to guide an introducer 70 as described below along an advancement axis into the field of view FOV of the imaging system 25 so that a professional can steer the introducer to a preselected location in the airway of a subject. The guide conduit 40 can include an entrance 42 and an exit 44. The entrance can be located at or near the attachment end 19 of the laryngoscope guide 10. The entrance can be oriented and sized to enable a corresponding introducer 70 to be inserted and subsequently moved, for example, by sliding the introducer 70, in the guide conduit 40. In use, the introducer 70 can be inserted in and moved in the guide conduit before, during or after a professional engages the blade of the guide with portions of the subject's anatomy.

The exit 44 can be disposed at or near the blade tip 11, generally forward of the viewing window 16 of the imaging element portion 14 and/or the imaging system 25, so that an introducer 70 projecting out from the exit 44 is within the field of view FOV at some point of advancement of the introducer and can be viewed by a viewer of the laryngoscope screen 24 (FIGS. 1 and 6). Of course, if desired, the exit 44 can be disposed adjacent or behind the viewing window 16 and/or imaging system 25 a preselected distance if desired in a particular application.

As shown in more detail in FIG. 7, this embodiment includes an exit end 45 and exit 44 positioned a distance D2 forward of the imaging system 25. This distance D2 can be optionally from 0.1 to 5.0 centimeters, further optionally about 0.25 to about 2.0 centimeters, or other distances as desired. With this forward positioning of the exit 44, the introducer 70 can be brought closer to the preselected location, or generally the target, before it exits the guide conduit 40. Accordingly, the guide conduit 40 provide the professional with slightly more steering control on the introducer 70. Optionally, the introducer enters the field of view FOV at a location relative to the imaging system that is near or adjacent the preselected location to facilitate insertion at the preselected location. With such a construction, the introducer has a relatively short distance to travel before it enters the preselected location and thus the possibility of it varying significantly from an intended trajectory, or off the advancement axis 52, is diminished. Of course, if desired, the exit 44 could be placed adjacent the imaging system 25 so that it does not extend any distance D2 forward of the imaging system 25. In yet other constructions, the exit 44 could be placed rearward of the imaging system 25. In these other embodiments, however, the guide might be modified to include other structures at or forward of the imaging system to assist in steering the introducer toward the target along a desired trajectory.

With reference to FIGS. 1-5, the guide conduit 40 can be a tubular element, such that it defines a bore 46. The bore 46 can be of any cross section, for example, circular, square, rectangular, triangular or other polygonal or other configurations. Generally, it has been found that the circular configuration is suitable because it tends to accept most introducers, including certain stylet rods that are also of a cylindrical or rounded construction. Further, the internal bore 46 of the guide conduit can be of various cross sectional dimensions, for example, about 10 mm to about 2 mm, optionally about 7 mm to about 4 mm and further optionally about 6 mm. The bore can be of other dimensions selected so that the introducer, also referred to as a guide member 70, can be inserted in and through the guide conduit 40.

In some constructions, the internal bore 46 can be lubricated with a lubricant, so that the introducer slides easily through it. The internal bore 46 can be coated with a coating that provides minimal friction to the introducer 70 sliding through it. Alternatively, the guide conduit 40 can be constructed from an extremely low friction material that facilitates sliding of an introducer 70 therethrough.

Optionally, the conduit 40 can be constructed to substantially circumferentiate or surround the outer dimensions of the introducer 70 when the introducer 70 or a section of the introducer is in the conduit 40. With such a construction, movement of the introducer 70 through the conduit 40 can be restrained so that the introducer moves primarily by sliding coaxially through the conduit 40. Further optionally, with such a construction, the conduit 40 can prevent or impair the introducer from being removed or displaced laterally outward from the conduit 40, for example, from a side or outer lateral portion 63, between the entrance and exit 44 of the conduit 40 when in use in a laryngoscopic or other procedure. In some cases, the circumferentiating or surrounding of the introducer by the conduit can be substantially complete, so that the introducer 70 is incapable of being removed from the lateral portion 63 of the conduit 40, but rather travels primarily only through the entrance 42 and/or exit 44 of the conduit to be removed from the conduit 40. This can prevent or impair the introducer 70 from becoming misguided or otherwise disengaging or dislodging from the conduit 40 when moving through the conduit or when positioned at rest at least partially in the conduit 40.

Further, as used herein, "incapable of being removed laterally" from the conduit or a component generally means that the introducer is not removable laterally from the conduit or component during normal use of the laryngoscope guide, that is, while it is being used in to perform laryngoscopy or some other procedure, such as those described herein, in or on a subject. The foregoing, however, does not preclude the introducer from being removed from the conduit via the exit or entrance of the conduit, nor does it preclude the introducer from being removed laterally from the conduit or a component when the laryngoscope is not being used in a laryngoscopic or other procedure in or on a subject. With regard to the latter, the conduit and/or lateral portion can define slots or holes through which a user can pull the introducer laterally outward from the conduit while the guide is located out of the subject and/or is not being used in a laryngoscopic or other procedure in or on the subject. Of course, if desired in other constructions, the guide 10 can be configured so that the introducer can be removed from the conduit in other manners. Further, the conduit 40 as shown, or in certain constructions, the conduit 40 can include apertures or recesses or slots so that the introducer is not always completely circumferentiated by the bore or conduit while in the conduit 40.

If desired, the internal bore 46 can extend from the entrance 42 to the exit 44. The entrance and exit can be located at opposite ends 45 and 47 of the conduit 40. In some cases, the internal bore can be closed off between the ends, so that the internal bore opens to the environment only at the entrance 42 and the exit 44 located at opposite ends of the conduit.

The introducer 70 used in the embodiments herein can be a solid stylet or rod, or a catheter or tubular type rod or cannula having a cross sectional dimension less than or equal to the cross sectional dimensions of the internal bore 46 of the guide conduit 40. The introducer 70 can also be of a flexible, non-rigid construction which is readily bent or misformed under slight force, much unlike rigid stainless steel guide elements for endotracheal tubes. The introducer can be flexible enough so that as it is moved in the conduit, it can bend and deform to follow the internal contours of the conduit, again, optionally unlike rigid stainless steel guide elements.

The introducer 70 can include a proximal end 71 and a distal end 75 with a primary portion 73 extending therebetween. The distal end 75 can generally be the end that is inserted first into the conduit 40. In many cases, the introducer can be of sufficient length so that the proximal end 71 does not enter the conduit as the introducer is advanced toward the preselected location, and remains graspable by a professional to manipulate the introducer 70. Optionally, the introducer 70 can be constructed to have a memory so that it can be bent or formed in a certain configuration and return to that configuration after undergoing certain forces. As an example, the introducer of U.S. Patent Publication 2008/0230056 to Boedeker, which is hereby incorporated by reference, can be used with the laryngoscope guide and methods herein if desired. Of course, other introducers can be used as well.

Further optionally, the introducer 70 can be configured in the form of a lumen and designed to be able to deliver a fluid, such as a gas, like oxygen, to a subject. In certain circumstances, where the laryngoscope guide herein is used to intubate a subject who needs oxygen or other gases as quickly as possible, such an introducer can be used to deliver those gases until the intubation tube is fully installed using the introducer.

Returning to FIGS. 2-5, the internal bore 46 can include internal surfaces and contours which are adapted to engage the introducer 70 when moved through it. These internal contours generally can follow the contours of the guide from the entrance to the exit of the conduit 40. Optionally, the guide conduit 40 can be of an arc shape, generally following the contour of an imaging portion 14 and transitioning toward and/or over the blade 12. When so configured, the internal surfaces of the conduit 40 also can be of an arc shape, which can cause the introducer when moved or slid through the internal bore to conform to that arc-shape. Where the introducer is generally linear before introduction into the conduit, the conduit and its internal contours can act on the introducer to temporarily or permanently bend it and conform to those contours at least as the section of the introducer is engaging those contours and passing through the conduit. When the introducer 70 exits the conduit 40 though the exit 44, the introducer optionally can unbend, extend or reconfigure itself wholly or partially back to its linear configuration. Of course, where the introducer 70 has a certain memory, and a professional preformed the introducer 70 before inserting it in the conduit 70, the introducer 70 can regain that previous preformed configuration.

Referring to FIGS. 3 and 4, the guide conduit 40 can include an entrance 42, noted above, which can terminate at or adjacent the attachment end 19 of the laryngoscope guide blade. Depending on the application, the end 47 of the guide conduit 40 adjacent the entrance 42 can be offset at an angle α, which can range from 0° to 60°, optionally about 10° to about 40°, or any other angle as desired for a particular application, from the axis 27 of the attachment end 19. Of course, if desired, the end 47 adjacent the entrance 42 can be parallel to the exit axis 27 if desired. Optionally, the entrance end 47 of the guide conduit 40 can be configured to extend beyond the terminal end 19 of the laryngoscope guide 10. In certain applications, the entrance end 47 can be flush with the end 19, or can terminate short of the end 19 a preselected distance.

As shown in FIGS. 3-7, the exit 44, and more generally the exit end of the conduit 40 can be oriented so that it advances and introducer exiting therefrom along an advancement axis 52. The advancement axis 52 generally can be oriented or arranged in a variety of configurations relative to various reference planes and axes as described herein. In general, the advancement axis 52 can be configured so that it is aligned to intersect one or more of the optical axis 25A of the imaging system 15, the midline 37 of the blade and the first blade plane 36. When such a configuration is utilized, the introducer 70 advanced along at least a portion of the advancement axis 52 is brought into the field of view of the imaging system in a manner that facilitates good viewing, aiming and/or steering of the introducer toward a preselected location. This, in turn, can improve the time to insert the introducer at the preselected location, and subsequently improve time to intubation of the subject.

For example, the exit end 45 or guide conduit 40 near the exit end can include a somewhat curved and/or angled configuration so that as an introducer 70 projects from and/or is advanced through the exit end 45 of the conduit 40 along a trajectory, it can tend to follow the advancement axis 52. In some cases, the curved or angled configuration of the guide conduit 40 or exit end 45 can impart a force or bending moment on the introducer to so that the introducer follows a corresponding curve or angle. The introducer 70 can follow such a curve or angle when advancing along a portion or along the entirety of the advancement axis 52. Optionally, the advancement axis 52 can be generally linear, as shown in FIGS. 3, 6, 7 and 12 or it can be curvilinear, such that it follows a simple or compound arc, which may be determined based on the configuration of the exit end 45 or guide conduit 40. Further optionally, the introducer 70 can include certain preformed bends or curves in the introducer 70 so that as the introducer extends from the exit, it follows the advancement axis 52 defined by the conduit 40, the exit end 45 and/or the exit 44 along a portion of that axis, but then deviates from the axis and follows its own trajectory.

As shown in FIG. 7, the relationship between the advancement axis, the blade plane 36, the midline 37 and the optical axis 25A of the illustrated embodiment will now be described. In particular, as mentioned above, the optical axis 25A extends or projects generally within the field of view FOV. The guide conduit 40 can be aligned so that the advancement axis 52 projects at a first angle $\Psi$ relative to the optical axis 25A and is oriented to traverse the optical axis 25A. This first angle $\Psi$ may be within a range having a lower limit of about 1°, 2°, 3°, 4°, 5°, 6°, 7°, 8°, 9°, 10°, 15°, 25°, 30°, 35°, and an upper limit of 35°, 30°, 25°, 20°, 15°, 10°, 9°, 8°, 7°, 6°, 5°, 4°, 3°, 2°, 1°. Optionally, the first angle $\Psi$ can be about 1° to about 25° and selected so that the introducer enters the field of view FOV laterally relative to the imaging system 25 from either lateral portion of 91, 92 of the field of view FOV as shown in FIG. 6. The orientation of the advancement axis 52 can be such that the professional, when viewing a monitor of the laryngoscope can obtain a clear view of a distal end 75 of the introducer 70 and advance and steer the introducer 70 along the axis toward the selected location, which again can be the opening 97 within the vocal folds 98 and into the trachea 96, during an intubation procedure. Of course, where the trajectory of the introducer 70 deviates from the advancement axis 52, the general alignment of the advancement axis 52 and optical axis 25A can still yield a beneficial view of the introducer within the field of view to help align and steer it with the opening 97.

As mentioned above, the advancement axis 52 can be oriented to traverse the optical axis. As used herein, traverse means cross when viewed generally from the view shown in FIG. 7, and does not necessarily mean that the advancement axis intersects the optical axis 25A. For example, the advancement axis 52 can project above or below the optical axis 25A depending on its orientation. Of course, in certain circumstances it also can precisely intersect the optical axis 25A. Generally, the advancement axis 52 can traverse the optical axis 25A forward of the distal tip 11. For example, the advancement axis 52 can traverse the optical axis 25A generally at point 51a forward of the distal tip 11. The precise distance forward of the distal tip 11 can range optionally from about 1 to about 15 centimeters, further optionally, about 2 to about 10 centimeters, even further optionally, about 3 to about 10 centimeters forward of the distal tip 11. Of course other distances can be selected as desired.

As further illustrated in FIG. 7, the advancement axis 52 can also be aligned to traverse the midline 37 and/or intersect the first blade plane 36. For example, the advancement axis 52 can be at some preselected angle γ relative to the first plane 36 and/or midline 37. Optionally, this angle γ, may be within a range having a lower limit of about 1°, 2°, 3°, 4°, 5°, 6°, 7°, 8°, 9°, 10°, 15°, 20°, 25°, 30°, 35°, and an upper limit of 35°, 30°, 25°, 20°, 15°, 10°, 9°, 8°, 7°, 6°, 5°, 4°, 3°, 2°, 1°. Further optionally, this angle γ can be in a range of about 2° to about 20°, even further optionally about 2° to about 10°. Of course other angles can be selected as desired and as described in further embodiments below.

The angle can be selected so that the introducer 70 enters the field of view FOV at a location so a professional can quickly view and understand the spatial orientation of the distal end 75 of the introducer 70 relative to the preselected location, for example, the opening 97 as shown in FIG. 6. The introducer can be advanced along the advancement axis 52 and can be aligned to traverse and/or intersect (which terms are used interchangeably when referring to blade planes herein) the first blade plane 36 or generally traverse the midline 37. Depending on the blade 12 configuration and the orientation of the field of view FOV in some circumstances, the introducer 70 may travel toward the first blade plane 36 and/or midline 37, but may or may not intersect these items before being inserted appropriately into a preselected location. Generally, if the introducer does intersect the first blade plane 36 and/or midline 37 while moving along the advancement axis 52, it can do so at a point 51B as shown in FIG. 7. This point 51B can be located forward of the distal tip 11 of the blade 12 a preselected distance, for example about 1 to about 15 centimeters, further optionally about 2 to about 10 centimeters, even further optionally about 3 to about 10 centimeters forward of the distal tip 11. With this distance, the introducer 70 typically will not completely overwhelm the field of view FOV of the imaging system 25. Accordingly, a professional can continue to view beyond the distal tip 11, for example, into the glottis 95 and more particularly the preselected location into which the introducer 70 and distal end 75 is desired to be inserted.

Optionally, as shown in FIG. 7, both the optical axis 25A and advancement axis 52 can be aligned to intersect the first blade plane 36 and/or traverse the midline 37 from opposite sides of those respective elements. In some applications the advancement axis and optical axis 25A can even be precisely oriented to intersect the blade plane at the same point. Alternatively, the advancement axis 52 and optical axis 25A can intersect the blade plane 36 at different points. Further optionally, at least one of the optical axis 25A and advancement axis 52 can be aligned to intersect the first blade plane 36. Of course, in some applications, the axes can be aligned so that neither the advancement axis 52 or optical axis 25A may intersect the first blade plane 36 and/or generally traverse the midline 37.

In the current embodiment shown in FIG. 12, the conduit 40, exit end 45 and/or exit 44 can be arranged so that the advancement axis 52 is disposed at a second angle ϕ relative to the second blade plane 54. At this second angle, the advancement axis 52 can diverge away from the blade 12 and optionally the superior portion 15 of the blade. Thus, when advanced along the advancement axis 52, the introducer will likewise diverge from the blade and optionally the superior portion of the blade. The second angle Ø can be in a range having a lower limit of 1°, 2°, 3°, 4°, 5°, 6°, 7°, 8°, 9°, 10°, 15°, 20°, 25°, 30°, 35°, 45° or 50° and an upper limit of 50°, 45°, 40°, 35°, 30°, 25°, 20°, 15°, 10°, 9°, 8°, 7°, 6°, 5°, 4°, 3°, 2°.

The second angle Ø can be precisely selected so that the advancement axis 52 is aligned with, and optionally parallel to, the laryngeal axis LA of the subject while the blade 12 is engaged against tissue, for example, the tongue and/or the epiglottis in the airway of the subject generally establishing a viewing volume 38. With such an alignment of the advancement axis 52 and the laryngeal axis LA, the introducer 70 generally follows the laryngeal axis LA, and can be precisely inserted in the opening 98 and trachea 96. Optionally, the second angle Ø can depend on the blade 12 configuration and/or the angle of the blade 12 relative to the remainder of the guide 10, which may or may not affect the alignment of the advancement axis and the laryngeal axis LA.

In the embodiment shown in FIG. 3, the conduit 40, exit end 45 and/or exit 44 can be arranged at some different angles relative to the second blade plane 54 to establish alternative advancement axes, for example advancement axes 52A or 52B. As an example, the exit 44, and more generally the conduit 40 can be aligned with the blade 12 so that the advancement axis 52B passes through or traverses the blade plane 54 at some location forward of the tip 11. In such an arrangement, the advancement axis 52B and subsequently the introducer 70 can converge toward the blade plane 54. As another example, the exit 44, and more generally the conduit 40 can be aligned with the blade 12 so that the advancement axis 52A is generally parallel to the blade plane 54. In such an arrangement, the advancement axis 52A and subsequently the introducer 70 can remain generally parallel to the blade plane 54, at least until the introducer passes beyond the distal tip 11 of the blade. Optionally, depending on the configuration of the blade, in some cases the advancement axes 52A and 52B also can generally align with the laryngeal axis of the subject while the blade engages the tissue in the airway.

As shown in FIG. 5, the guide conduit 40 can extend toward the tip 11, generally within the perimeter defined by the laryngoscope blade 12. The exit end 45 and the exit 44 can be configured so that they are located within the lateral boundaries or dimensions 56 of the blade 12. In certain circumstances, the end 45 and the exit 44 can be displaced a distance D inward from the outermost lateral dimensions 56 of the blade 12. Accordingly, the end 45 and the respective exit 44 can be restricted from contacting tissue laterally beyond the dimension 56 of the blade 12, and generally beyond the lateral and medial portion 32, 33 of the blade, when the laryngoscope guide 10 is inserted into the subject.

The guide conduit 40 can include a major portion 41 and a minor portion 43. The minor portion 43 can be immediately adjacent and can form a portion of the exit end 45. The minor portion 43 can be angled as shown in phantom lines at 45a in FIG. 5, toward the optical axis 25A, or more generally the first blade plane 36 and/or midline 37. This construction can facilitate viewing of the exit 44 of the guide conduit 40, as well as viewing of the introducer 70 and distal end 75 of the introducer extending therefrom toward the aforementioned optical axis 25A, first blade plane 36 and/or midline 37. The minor portion 43 can be disposed at a third angle Ω relative to the major portion 41. This third angle can be in a range having an lower limit of 1°, 2°, 3°, 4°, 5°, 6°, 7°, 8°, 9°, 10°, 15°, 20°, 25°, 30°, 35° and an upper limit of 35°, 30°, 25°, 20°, 15°, 10°, 9°, 8°, 7°, 6°, 5°, 4°, 3°, 2°, 1°. The transitions between the major 41 and minor 43 portions can be abrupt and angular as illustrated, or can be curved and transition gradually. Optionally, when the introducer 70 advances from the major portion 41 to the minor portion 43 through the conduit 40, the internal contours and bore of the conduit 40 can impart a bending force on the flexible introducer. In some constructions, this bending force can assist in aligning the trajectory of the introducer 70 with the advancement axis 52.

The guide conduit 40 can be an integral portion of the laryngoscope guide blade 10. For example, it can be integrally molded with the other components of the guide blade 10. Alternatively, it can be a separate tube that is removably or non-removably coupled to the exterior of the laryngoscope guide blade 12. As an example, the guide conduit 40 can be a portion of a polyvinyl chloride tube that is adhered, glued, riveted, fastened, hot melted, ultrasonic welded, spin melted, vibration melted, radio frequency melted, laser melted or otherwise joined with the laryngoscope guide blade 10. Optionally, the guide conduit 40 can be configured so that it does not advance or guide or hold a conventional endotracheal tube, let alone an endotracheal tube including a cuff, as the cuff could be difficult to advance through the conduit, and when placed forward of the imaging system, could obscure the field of view.

Optionally, the laryngoscope guide 10 can be operable in first and second modes in which the guide 10 can be used to install the introducer 70, and to remove the guide 10 leaving the introducer in place, respectively. In the first mode, the introducer 70 can be guided by the conduit in manners described herein, toward any of the respective axes or lines. In this mode, the distal end of the introducer can generally enter the preselected location, for example, the glottis or trachea entrance. In the second mode, the laryngoscope guide 10 can be removed from the subject, leaving the introducer distal end in place, in the preselected location. In the second mode, as the guide is being removed, the introducer 70 and conduit 10 can slide coaxially relative to one another as described herein. With the guide removed, the endotracheal tube 80 can be placed on and guided by the introducer as described herein to intubate the subject.

In general, the guide 10 and its components can be constructed from a variety of materials, such as elastomers, rubbers, plastics, polymers, composites, metals, or combinations of the foregoing. The guide and its components can be injection molded and/or machined, depending on the material used. Further, although shown as a guide that is removable from the laryngoscope 20, the guide 10 can form an integral part with the remainder of the laryngoscope 20, depending on the application.

II. Methods of Use

Figure 11:
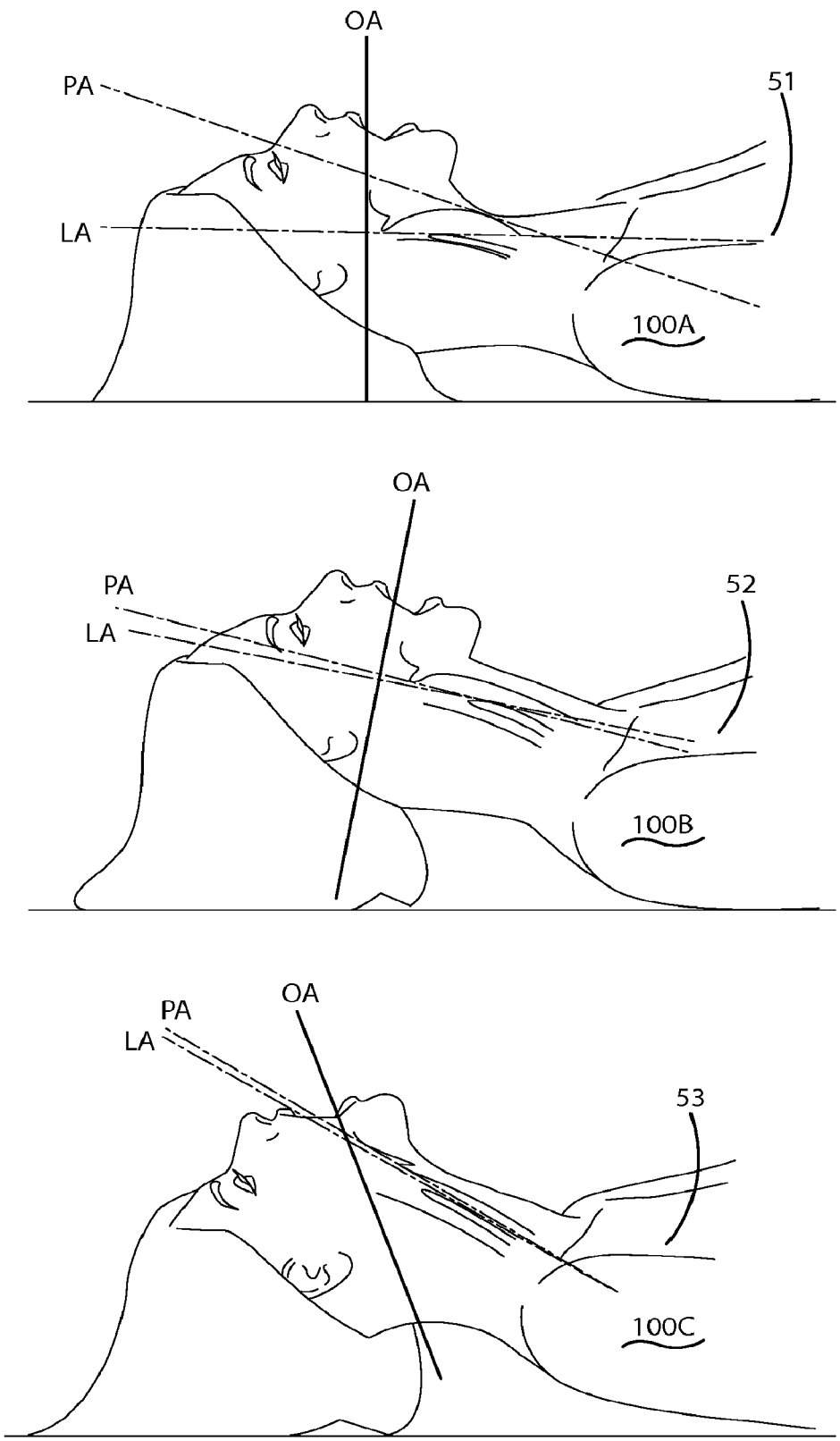
FIG. 11 is a side view of different positions of a subject's head and the relative alignment of an oral axis, a pharyngeal axis and a laryngeal axis of the subject.

A method of using the laryngoscope guide 10 of the current embodiment will now be described with reference to FIGS. 11-17. To begin, the laryngoscope guide 10 and method described herein can be used where the subject's head and airways are in a variety of positions. Some suitable positions are shown in FIG. 11. There, the subject 100A is shown in a substantially neutral supine position. In such a position, the oral axis OA of the subject 100A is misaligned substantially with both the pharyngeal axis PA and laryngeal axis LA. For example, the oral axis OA can be at an angle of about 60° to about 90° relative to the pharyngeal axis PA and about 70° to about 90° or more, relative to the laryngeal axis LA. Before the present laryngoscope guide 10 and method, this orientation in the neutral position was difficult to intubate because the laryngeal axis LA, pharyngeal axis and oral axis are substantially misaligned which can make it difficult to steer an endotracheal tube into the trachea of the subject. With the laryngoscope guide methods described herein however, this obstacle is overcome and patients in this neutral position can easily be intubated.

Returning to FIG. 11, the subject 100B is shown with their head elevated, with the oral axis OA substantially misaligned with both the pharyngeal axis PA and the laryngeal axis LA, however, the pharyngeal axis PA and laryngeal axis LA are generally aligned with one another. The laryngoscope guide and methods herein are also well suited to be used on the subject of the type 100B if desired.

FIG. 11 also illustrates a subject 100C with the neck and head extended to align the oral axis OA with the pharyngeal axis PA and the laryngeal axis LA. Generally, the oral axis OA is about 30° to about 60° angle relative to the pharyngeal axis PA and/or laryngeal axis LA. With this alignment of the relative axes, a user can obtain a rather direct view of the glottis to facilitate intubation. Of course, the laryngoscope guide and related methods herein are well suited to intubate a subject 100C as shown in FIG. 11, and any other subjects in virtually any other positions.

Figure 13:
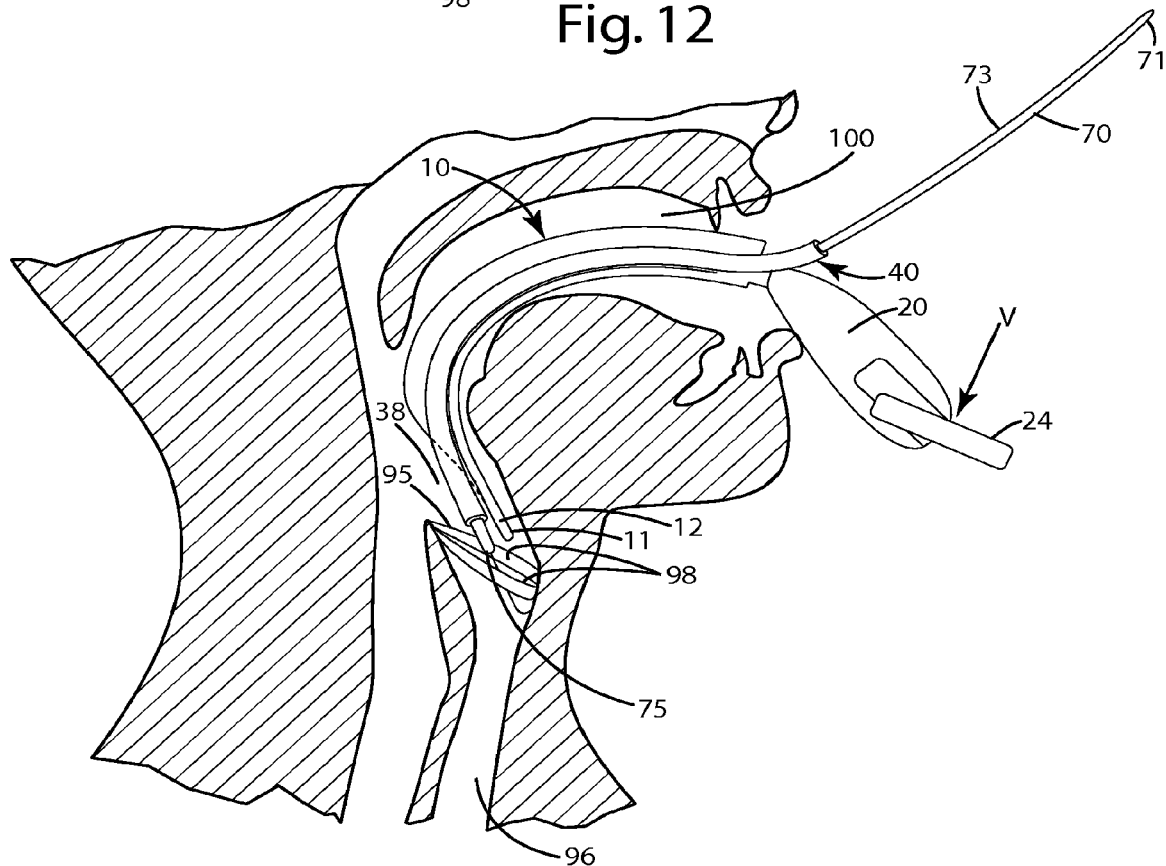
FIGS. 13-17 are cross section views showing the use of the laryngoscope guide of the current embodiment.

Intubation of a supine subject 100, with their head in a neutral position, with their oral axis substantially misaligned with both the pharyngeal axis and laryngeal axis, will now be described. As shown in FIG. 13, the laryngoscope 20 and the associated laryngoscope guide is inserted in the subject's oral cavity. In this position, the health professional V manipulating the laryngoscope 20 can view the monitor 24 which offers a view of the glottis and assist in steering the introducer 70 within the glottis 104 and generally into the trachea 108. Optionally, before inserting the laryngoscope 20 and the respective guide 10 into the subject 100, where the laryngoscope guide 10 is a disposable unit or generally removable relative to the laryngoscope 20, that laryngoscope guide 10 can be installed and generally secured to the guide attachment end of the laryngoscope 20. Of course, where laryngoscope guide is not of a removable or disposable type, this step can be eliminated. Further optionally, if the introducer 70 is constructed to have a memory, the professional optionally can perform or otherwise bend the introducer at certain locations along the introducer with the expectation that after the introducer exits the exit of the laryngoscope guide 10, those preformed structures or bends can assist in locating and/or steering the introducer 70 to the preselected location.

Upon initially inserting the laryngoscope guide 10, the professional V can use the blade 12 of the laryngoscope guide to engage the tongue and/or epiglottis with a force sufficient to move the tissue at issue and establish a viewing volume 38 within the subject's airway. The distal tip 11, and more generally the blade 12, can be manipulated so that the glottis 95 is within the field of view FOV of the image system of the laryngoscope 20. The image data concerning the glottis, for example the image of the glottis as shown in FIG. 6, can be communicated to the monitor 24 as the procedure continues. The laryngoscope blade 12 can be positioned with the assistance of the professional V viewing the screen 24 (FIG. 1) of the laryngoscope 20. The distal tip 11 of the blade can be positioned short of the subject's vocal chords 98, adjacent the glottis 95. The introducer 70 and more specifically, the distal end 75, can be inserted first into the guide conduit 40. Optionally, before insertion into the guide conduct 40, the introducer 70 can be lubricated with a sufficient lubricant to facilitate movement of the introducer 70 through the guide conduit 40. As shown in FIG. 6, the introducer 70 can be aligned so that the distal end 75 lays along the advancement axis 52 and is configured to traverse the alignment axis 25A. The alignment axis 25A can be, or more generally the field of view FOV can be aligned, so that the introducer 70 is aimed into the opening between the vocal folds 98 generally into the trachea 96 with the objective being insertion of the distal end 75 of the introducer 70 into the opening 97 and optionally a preselected distance into the trachea 97.

Figure 14:
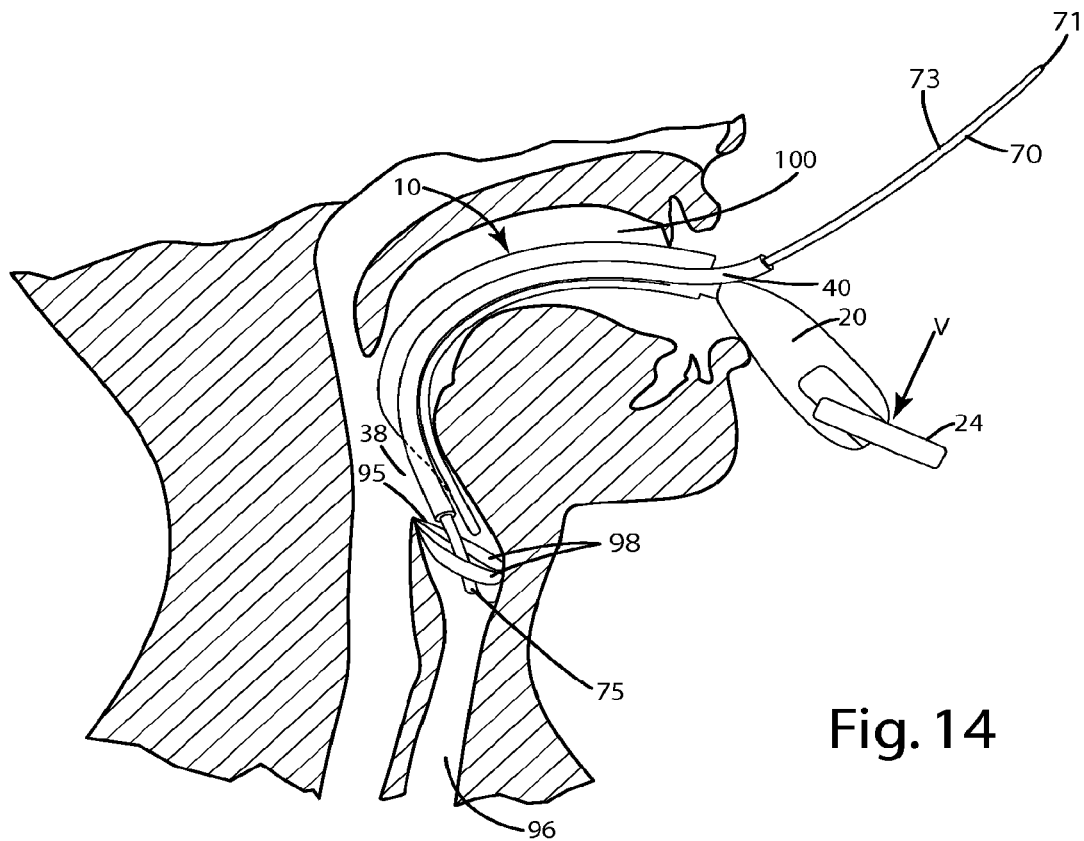

As shown in FIG. 14, the professional V advances the introducer 70 so that it slides coaxially within the guide conduit 40. Because the illustrated introducer 70 is flexible, it generally bends and conforms to the contours of the guide conduit 40 as it is forced through the conduit 40. The introducer continues to flex and flexibly conform to the internal contours of the guide to it and follows the conduit until the distal end 75 exits the conduit 40 at the exit 44 of the conduit 40. The professional V can view the advancement of the end 75 on the monitor of the laryngoscope 20.

With reference to FIG. 6, as the introducer end 75 is advanced along the advancement axis 52, the professional can manipulate the guide 10 which in turn adjusts the conduit 40 and the associated advancement axis 52. This can subsequently assist in steering the distal end of the introducer 75 into the desired preselected location which corresponds to the opening 97. The professional aligns the introducer distal end 75 with the glottis and more particularly with the opening 97 and trachea 96. The advancement of the introducer 70 in the field of view FOV continues so that the distal end 75 inserts or otherwise enters the opening 97 and enters at least a portion of the trachea.

The end 75 is further advanced until it is at least partially within the trachea 96. Generally during or before this particular juncture, the introducer 70 is aligned to intersect the first blade plane 36 and/or traverse the optical axis 25A and/or midline 37 as shown in FIG. 7. With this advancement, the professional can maintain a good view of the distal end 75 of the introducer and steer it towards a desired location. Further, where the conduit is constructed as shown in FIG. 12, during this advancement the introducer 70 can generally diverge from the second blade plane 54. In turn, the introducer 70 can align with the laryngeal axis LA to further facilitate insertion of the distal end 75 in the opening in the trachea 96.

Returning to FIG. 15, with the end 75 located at or within the trachea 96, the laryngoscope 20 and the laryngoscope guide 10 can be removed from the subject's airway. In doing so the professional grasps the proximal end 71 or primary portion 73 of the introducer to maintain the distal end 75 in the trachea 96 or other preselected location. With the introducer 70 being so held in place, the user then draws the guide 10 out from the subject's airway and mouth. During this action, the guide conduit 40 slides relative to the introducer 70. Accordingly, the introducer 70 flexibly conforms to the internal contours of the conduit 40 as the conduit is removed from the introducer. Generally, the guide conduit 40 slides coaxially relative to the introducer 70 as it is removed. The conduit 40 is further slid past and over the proximal end 71 of the introducer 70. Generally during the entire process of the removal, the professional or an assistant holds the introducer 70 so that the distal end 75 does not move and generally maintains its position within the trachea or other preselected location.

Figure 16:
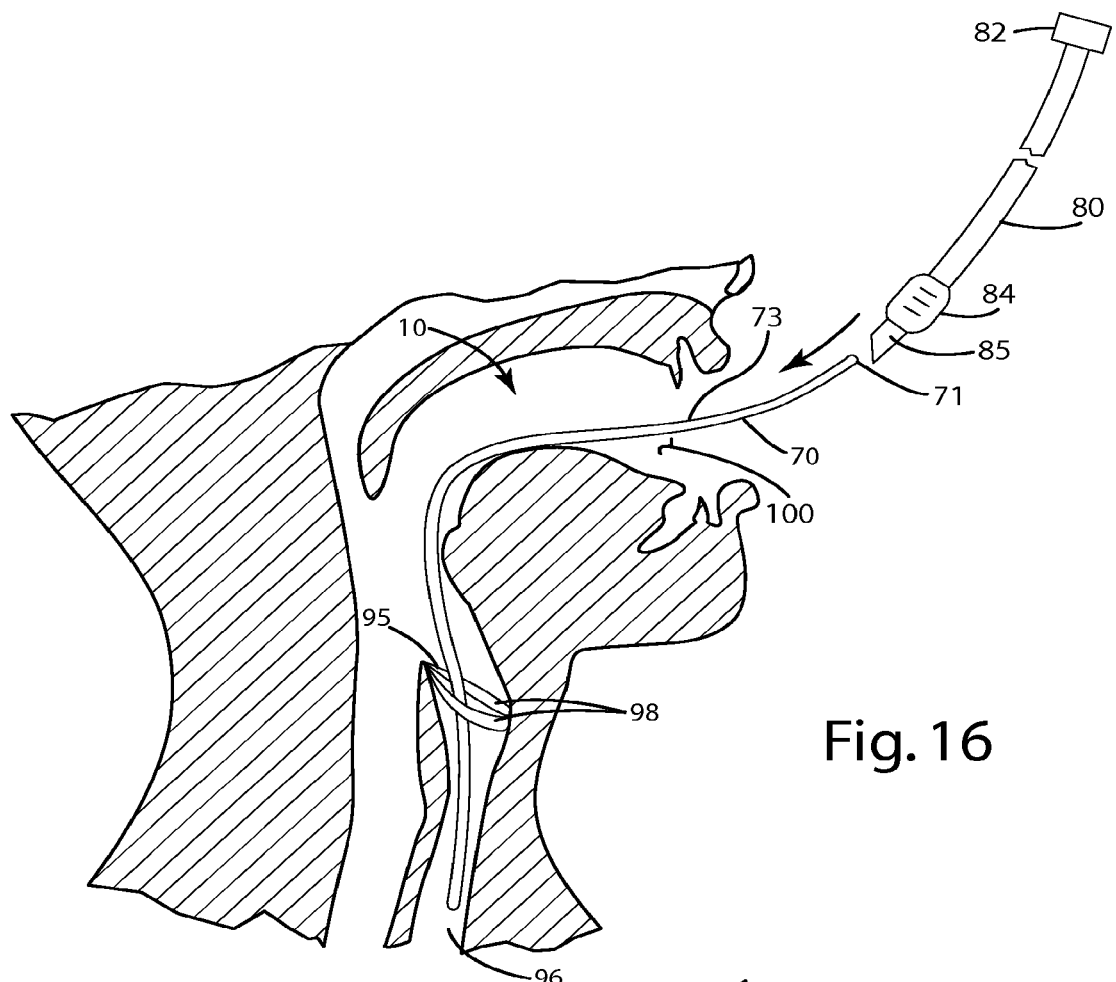

After the laryngoscope guide 10 is removed from the introducer 70, the introducer 70 remains in the subject 100 as show in FIG. 16. The professional then readies an endotracheal tube 80 to be guided by the introducer 70 to the patient's trachea. While the endotracheal tube 80 can be of a variety of configurations, it generally includes a tube end 85 or distal tube end also referred to as a distal tube end, a cuff 84, and a connector end 82. The cuff 84 can be designed to inflate or otherwise extend within the trachea 96 of the subject to seal the trachea around the tube. The connector end 82 can be connected to a source of gas, for example oxygen to ventilate the subject or an anesthetic or other therapeutic gas.

The professional positions the endotracheal tube 80 and coaxial arrangement relative to the proximal end 71 and primary portion 73 of the introducer. With this arrangement, the professional then slides the endotracheal tube 80 along the introducer 70. With this arrangement, the introducer 70 guides the tube end 85 directly to the trachea 96. The endotracheal tube 80 continues to be advanced until it enters the glottis 95, and more particularly inserts at the opening 97 and projects into the trachea 96. Optionally, in some cases the endotracheal tube may have a significantly larger diameter than the introducer, in which case the respective longitudinal axes of the introducer 70 and the endotracheal tube 80 are not perfectly aligned. Nonetheless, the introducer and endotracheal tube are still considered to be in a coaxial arrangement and adapted to coaxially move and/or slide relative to one another.

Figure 17:
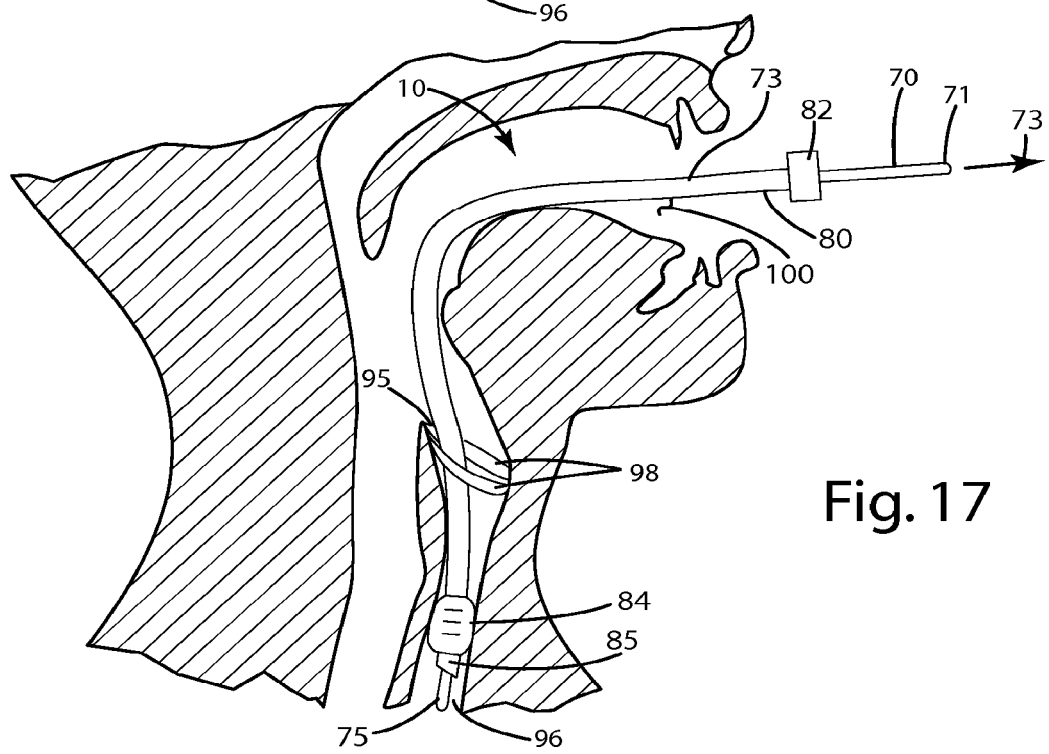

As shown in FIG. 17, the endotracheal tube is fully guided to the trachea 96, with the tube end 85 being near or adjacent the introducer end 75. Where the endotracheal tube 80 includes a cuff 84, the cuff can be inflated to seal off the trachea. The introducer 70 then can be removed from the glottis 95 and more particularly slid coaxially outward from the endotracheal tube 80 as shown by the arrow. The entire introducer 70 can be removed from the tube 80. After this is accomplished, the endotracheal tube 80 can be connected to a source of gas as mentioned above or otherwise used to utilize to establish an airway for the subject.

Although including the steps of introducing the introducer, removing the laryngoscope guide, and guiding the endotracheal tube with the introducer, the above method of use of the laryngoscope guide can significantly reduce the amount of time to intubation. Further, this also can assist both inexperienced and experienced care professionals in intubating subjects who are typically considered impossible to intubate or generally extremely difficult to intubate. For example, the laryngoscope guide and methods can be used to intubate subjects who have limited mobility, and can only be intubated while their head is in a neutral position. This can be particularly helpful where the subjects are obese. The guide and method can be used to directly intubate an obese subject who may have a short, thick and sometimes immobile neck, a large tongue, and/or redundant folds of oropharyngeal tissue. In such subjects, placing an endotracheal tube can be extremely difficult due to the obstruction caused by the extra tissue in the airway. With the present guide and method, the introducer can be introduced into the glottis, and more generally the trachea, without becoming lost in the extra tissue, generally because the introducer is guided through that tissue to the glottis, through the guide conduit of the laryngoscope guide. Further, the introducer can act as a reliable guiding mechanism for an endotracheal tube so that the tube does not readily become hung up on the extra oropharyngeal tissue. Accordingly, the laryngoscope and related method can provide assistance in intubating obese and morbidly obese subjects.

In addition, the laryngoscope and related guide and method of use can be used to intubate subjects that only can be intubated with their heads in a neutral head position, for example, subjects who have undergone trauma requiring a cervical spine collar, subjects who have arthritis or mandibular fractures, or subjects who have had previous cervical fusion, as well as subjects who are simply combative. The laryngoscope guide and related methods can be used to intubate any of these and other subjects with good expected results and a reduction in time to intubation.

While the laryngoscope guide and above methods are primarily directed to intubation procedures, the laryngoscope guide can be used in other procedures. In one procedure, the laryngoscope guide and method can be modified to acquire samples located within a patient's glottis, trachea, larynx, pharynx or other portion of their airway. For example, the laryngoscope guide 10 can be inserted into an airway of a subject, and operated to establish a viewing volume. The guide 10 can be aligned to obtain a field of view FOV of the glottis 95 and various components, similar to shown that in FIG. 6. However, instead of advancing an introducer through the guide element 40, a medical device, such as endoscopic biopsy forceps or some other retrieval device, can be inserted and coaxially advanced through the conduit 40. The distal end of the forceps including the arms can project from the guide conduit 40 along the advancement axis 50, all while being aligned with the various reference planes and axes described herein. The forceps can be used to collect a tissue sample from any anatomical feature within the field of view FOV. After the sample is collected, the forceps can be removed with the laryngoscope guide 10 from the subject. Alternatively, the forceps can be coaxially withdrawn through the guide 40 with the tissue sample likewise traveling through the guide conduit 40.

In another procedure, the laryngoscope guide and method can be modified to remove polyps or nodes from anatomical features, such as the vocal chords, the epiglottis, and the like. In such a procedure, the laryngoscope guide 10 can be inserted in the patient's airway as described in the methods above. However, instead of the introducer 70 being introduced into the field of view as shown in FIG. 6, a polyp snare, snipping device, clipping device or cutting device, can be advanced along the axis 52 in the manner that the introducer is advanced in any of the embodiments described herein. The snare or device can be positioned adjacent the polyp and actuated to remove the polyp. After the polyp is removed, the laryngoscope guide can be removed from the subject. Alternatively, the snare or device can be coaxially withdrawn through the conduit 40.

In yet another procedure, the laryngoscope guide and related methods can be modified to administer drugs, medicaments or agents (collectively, agents) directly to anatomical features within the subject. To do so, the laryngoscope guide 10 can be inserted in the subject's airway and operated in a manner similar to that of the embodiments above. Instead of the introducer advancing along the advancement axis 52, however, an endoscopic injection needle can be substituted in its place. The needle can be used to administer an agent to desired locations within the field of view FOV, while being steered as described above.

In a further procedure, the laryngoscope guide and methods can be modified to place an esophageal dilation balloon in a subject's esophagus. Again, the manner of placement would be similar to that of placing the introducer as described in the embodiments above, with the exception that instead of aligning and steering the introducer and components toward the trachea, the balloon would be steered to the desired location within the esophagus.

In yet a further procedure, the laryngoscope guide and related methods can be modified to perform surgical operations to correct anatomical defects, lacerations and/or trauma to the glottis, trachea, esophagus or other anatomical features. In such operations, the laryngoscope guide 10 could be inserted into the airway of the subject as described in the embodiments above. The introducer could be replaced with the appropriate surgical instrument and guided into the field of view FOV as shown in FIG. 6 so that the professional could manipulate the device and perform the desired procedure on the anatomical feature.

III. First Alternative Embodiment

Figure 8:
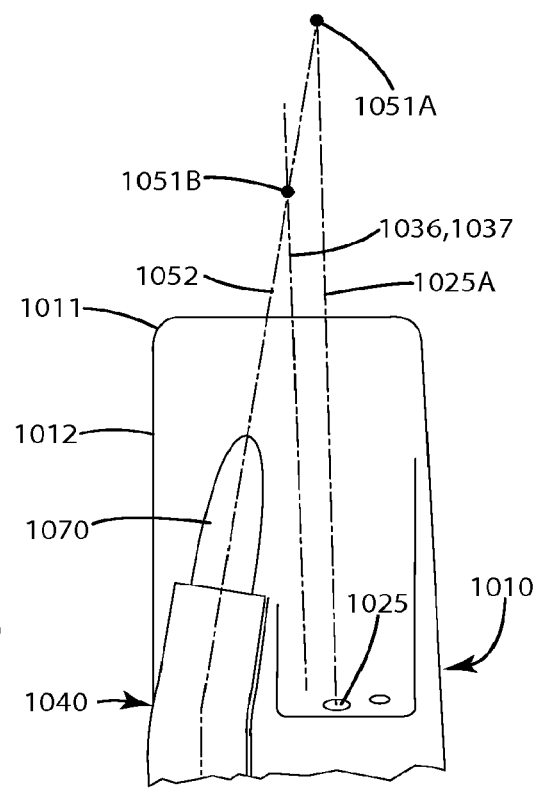
FIG. 8 is a top view of the laryngoscope guide of a first alternative embodiment illustrating orientation of certain axes and planes.

A first alternative embodiment of the laryngoscope guide is illustrated in FIG. 8 and generally designated 1010. The laryngoscope guide 1010 in this embodiment is similar to the current embodiment, with several exceptions. For example, the optical axis 1025A projects from the imaging system 1025 substantially parallel to the first blade plane 1036 and/or the midline 1037. Optionally, it may diverge from these reference elements. The advancement axis 1052 is aligned to intersect the first blade plane 1036 at the point of intersection 1051B. This point of intersection can be forward of the blade tip 1011 a distance as described in the embodiments above. Likewise, the advancement axis 1052 is aligned to traverse the midline 1037. The advancement axis 1052 can be oriented at angles similar to γ noted above in connection with the first embodiment shown in FIG. 7. Further, the advancement axis 1052 can be aligned to traverse the optical axis 1025A. This can occur at some point 1051A forward of the tip 1011 if desired. The angle at which the advancement axis 1052 traverses the optical axis 1025A can be similar to the angle Ψ discussed above in connection with the embodiment in FIG. 7. With this construction, the introducer 1070 advanced along the advancement axis 1052 can be viewed by a viewer via the imaging system 1025, aligned and steered using the methods herein.

IV. Second Alternative Embodiment

Figures 9, 10:
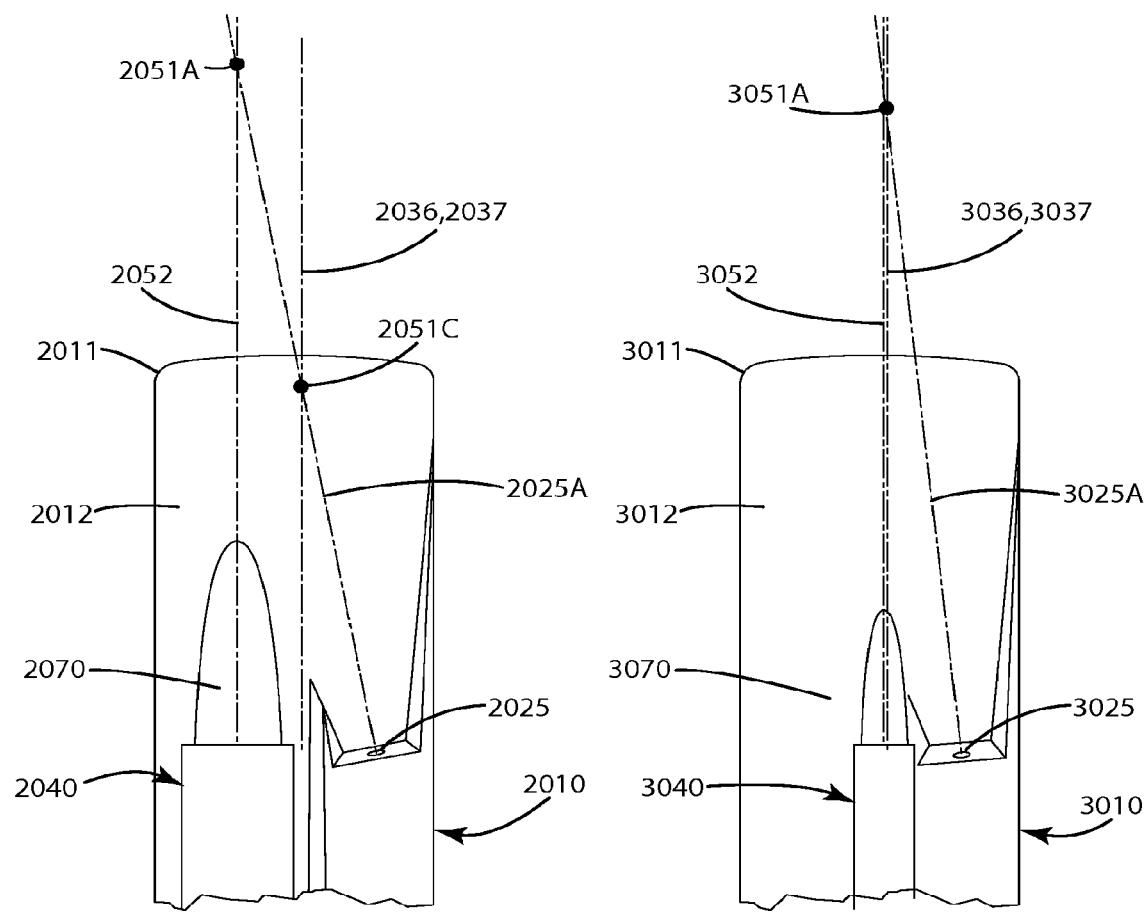
FIG. 9 is a top view of the laryngoscope guide of a second alternative embodiment illustrating orientation of certain axes and planes.
FIG. 10 is a top view of the laryngoscope guide of a third alternative embodiment illustrating orientation of certain axes and planes.

A second alternative embodiment of the laryngoscope guide is illustrated in FIG. 9 and generally designated 2010. This laryngoscope guide 2010 is similar to the above embodiments with several exceptions. For example, in this embodiment, the advancement axis 2052 is generally parallel to and/or diverges from the blade plane 2036, or generally does not traverse the midline 2037 forward of the distal tip 2011 of the blade 2012. The advancement axis 2052 can, however, be aligned so that it traverses the optical axis 2025A if desired. This traversing can occur at some point 2051A forward of the distal tip 2011 of the blade 2012. Of course, if desired, the point of traverse can occur rearward of the distal tip 2011, as with any of the embodiments herein.

The advancement axis 2052 and optical axis 2025A can be disposed relative to one another at angles similar to the angle Ψ described in the current embodiment above. The optical axis 2025A also can project toward and generally intersect the first blade plane 2036 and optionally traverse the midline 2037. This intersection and traversing can occur at some point 2051C, which can be rearward of the distal tip 2011 or forward of the distal tip 2011 as desired in the particular application.

In the embodiment shown in FIG. 9, the conduit 2040 can be aligned parallel to at least one of the first blade plane 2036 and/or the midline 2037. Accordingly, the introducer 2070 can travel along the advancement axis 2052 generally parallel to these components. Of course, the conduit 2040 alternatively can be angled outward away from the blade plane 2035 and/or the midline 2037, in which case, the introducer could generally diverge from those elements. As also shown in FIG. 9, the imaging element 2052 can be oriented so that the optical axis 2025A projects through the blade plane 2036, generally traverses the midline 2037. With this configuration, the introducer 2070 can be viewed along the advancement axis 2052 to align and optionally steer the distal end of the introducer 2070 to a preselected location.

V. Third Alternative Embodiment

A third alternative embodiment of the laryngoscope guide is illustrated in FIG. 10 and generally designated 3010. This laryngoscope guide 3010 is similar to the above embodiments with several exceptions. For example, in this embodiment, the guide conduit 3040 is positioned generally centrally relative to the blade 3012 of the guide 3010. Accordingly, the advancement axis 3052 is aligned with the first blade plane 3036 so that it is coincident with the first blade plane 3036. Optionally, the advancement axis 3052 can run parallel to the plane 3036. The axis 3052 also can be parallel to, and generally lay above the midline 3037.

The optical axis 3025A and advancement axis 3052 can intersect at some point 3051A forward of the distal tip 3011 of the blade 3012. Of course in the embodiment illustrated in FIG. 10, the first blade plane 3036 and optionally the midline 3037 can also intersect or traverse the optical axis 3025A at the location 3051A as well.

When the introducer 37 is advanced along the axis 3052 in the embodiment show in FIG. 10, the introducer 37 can generally intersect the blade plane 3036 along a line through the blade plane 3036. As also shown in FIG. 10, the imaging element 3052 can be oriented so that the optical axis 3025A projects through the blade plane 3036, generally traversing the midline 3037, so that the introducer 3070 can be viewed as it travels along the advancement axis 3052 to align and optionally steer the distal end of the introducer to a preselected location.

VI. Fourth Alternative Embodiment

Figure 18:
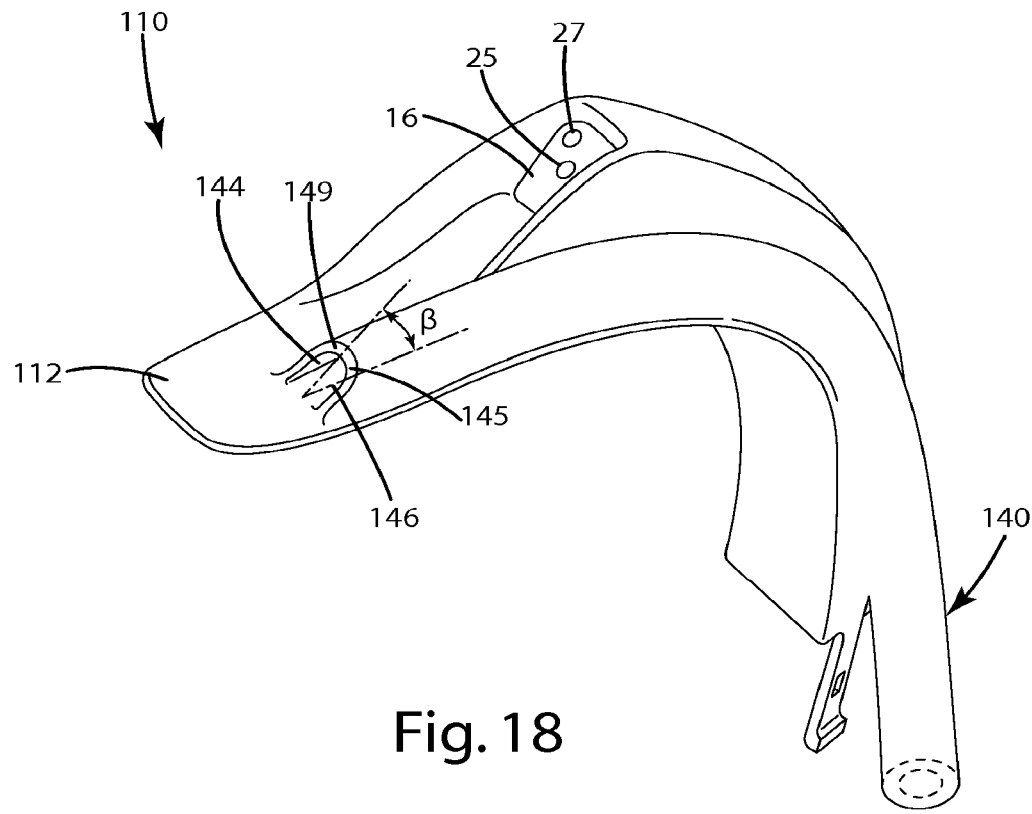
FIG. 18 is a perspective view of a fourth alternative embodiment of the laryngoscope guide.
Figure 19:
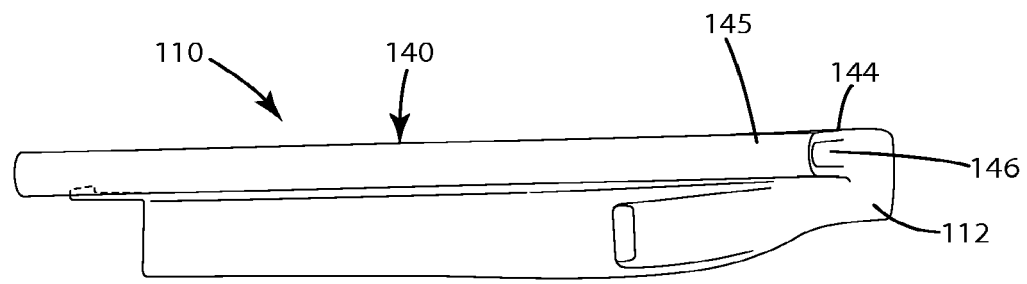
FIG. 19 is a top view of the fourth alternative embodiment of the laryngoscope guide.

A fourth alternative embodiment of the laryngoscope guide is illustrated in FIGS. 18 and 19 and generally designated 110. The laryngoscope guide 110 of this embodiment is similar to the current embodiment with a few exceptions. For example, the guide conduit 140 is more integrated into the blade 112. As shown, the blade 112 forms a lower portion of the internal bore 146 of the guide conduit 140. The exit end 145 and more particularly, the exit 144 can be of a lowered and/or angled or curved profile. For example, the outer edge 149 of the exit 144 can be at an angle β relative to the blade 112. This angle can range from 90° to 10°, optionally about 50° to about 20°, and further optionally about 40°. Optionally, this reduced angle can reduce tissue irritation when the guide 110 is inserted into the subject's mouth and/or throat. Of course, other low profile configurations can be used at this exit 144 to reduce the profile and further minimize a potential tissue disruption.

VII. Fifth Alternative Embodiment

Figure 15:
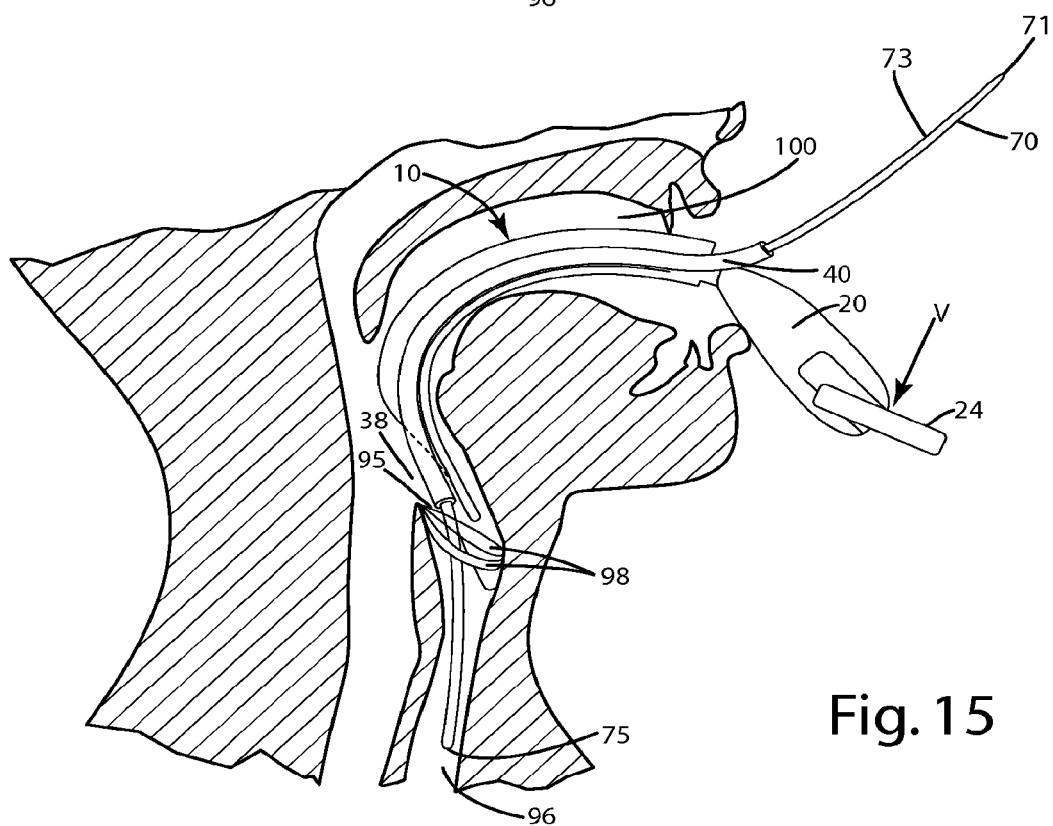

A fifth alternative embodiment of the laryngoscope guide is illustrated in FIGS. 20-23 and generally designated 210. The laryngoscope guide 210 of this embodiment is similar in construction and operation to the above embodiments with several exceptions. For example, as shown in FIGS. 13-15, the guide conduit 240 is pre-constructed as a tubular member having a corresponding curvilinear structure that matches a seat 218 of the guide 220. The guide conduit 240 can be pre-constructed and can be angled at a junction 256 between a major portion 241 and a minor portion 243 of the guide conduit 240. Optionally, the minor portion 243 can be angled at an angle Φ as illustrated in FIG. 22. This angle Φ can be 1°, 3°, 5°, 10°, 15°, 20°, 25°, 30°, or any other desired angle. With this optional angled minor portion 243, a guide element 70, shown in broken lines, can be advanced along a line of advancement 252. Optionally, this line of advancement 252 can be such that the guide element 70 transverses the field of view FOV of the imaging system 225 to provide a view of the guide element 70 to a professional as it is advanced to a preselected location as described above.

As shown in FIG. 20, the guide conduit 240 also can extend a preselected distance 267 beyond the rear portion 219 of the laryngoscope guide. This preselected distance 267 can be selected so that the entrance 242 of the guide conduit 240 is a satisfactory distance beyond the end of the laryngoscope guide connection portion 28 as shown in FIG. 1. It may also be predisposed at virtually any angle relative to the imaging section 214 or other portions or components of the laryngoscope guide 210.

The laryngoscope guide 210 can include a support base 255 that elevates the exit end 245 of the guide conduit 240 a preselected distance 257 above the laryngoscope guide blade 212, as shown in FIG. 21. The preselected distance 257 can be anywhere from 0.01" to 0.25" to 0.5" or any increment therebetween, depending on the particular application. The support base 255 can be a simple flange or plate that extends upward from the blade 212 as shown in FIGS. 20 and 21. Alternatively, the support base can be a more rigid member of a greater width and can extend across the entire bottom portion of the guide conduit 240 as desired. Generally, the support base 255 can assist in establishing an angle between an advancement axis 252 of the guide 240 and a second plane 254 of the blade, which can be any of the angles described in connection with the embodiments above. Moreover, like the embodiments above, the angle can be such that as an introducer 70 advances along the advancement 252 axis, it diverges from the plane, and generally aligns with a laryngeal axis of a subject.

As shown in FIGS. 22 and 23, the blade 212 can transition to a flange 217 that extends along side the imaging portion 214 of the laryngoscope guide. A guide conduit seat 218 can extend upward along a portion of the imaging portion 214 and optionally laterally outward onto the flange 217, and further optionally forwardly onto the blade 212 toward the tip. The portion 266 of the seat 218 that extends forwardly onto the blade 212 can be angled toward the FOV, optionally at the angle Φ described above in connection with the guide conduit 240. The seat 218 can be a geometry that matches the exterior surface of the guide conduit 240 as desired. With such a geometry, the seat 218 can readily match and enable the guide conduit 240 to fit closely against it, thereby providing a good joining surface between the guide conduit 240 and the components of the laryngoscope guide 210.

An exemplary method for constructing the fifth alternative embodiment also is provided. In this method, the body of the laryngoscope guide 210 can be injection molded to include the various components, including but not limited to, the imaging portion 214, the flange 217, the blade 212, the seat 218, and the angled portion of the seat 266. The portion of the mold that forms an internal cavity defined with an imaging section 214 can be withdrawn from the molded laryngoscope guide 210. This, of course, can leave a cavity within the imaging portion 214. The guide conduit 240 can be pre-constructed from PVC tubing or other materials, and formed to include certain contours matching the contours of the laryngoscope guide blade 210. One of these contours of the tubing can be the angle 256 between the minor portion 243 and the major portion 241 of the guide conduit 240. The guide conduit 240 can be joined with the laryngoscope guide 210 as shown in FIG. 22. There, the guide conduit 240 is mated with the seat 218 and the flange 217. The guide conduit can be joined with the laryngoscope guide 210 using ultrasonic welding, cement, adhesives, or any other joining techniques disclosed herein.

With the guide conduit 240 joined to the molded body of the laryngoscope guide 240, the laryngoscope guide and/or guide conduit can be further trimmed, polished or can undergo other finishing and packaging operations. Of course, other methods for manufacturing the laryngoscope guide, and joining the laryngoscope guide with the guide conduit 240 can be substituted for the method noted above.

VIII. Sixth Alternative Embodiment

A sixth alternative embodiment of the laryngoscope guide is illustrated in FIG. 24 and generally designated 310. The laryngoscope guide 310 of this embodiment is similar in construction and operation to the above embodiments with several exceptions. For example, the guide conduit 340 can terminate at the exit end 345 in an angled configuration. The exit end 345 can be formed so that the lower portion of the bore 346 is bounded by a lower portion 341 of the guide conduit, while the upper portion of the guide conduit 340 at the exit end 345 is removed. In effect, the guide conduit exit end 345 can be angled to create an open top configuration at the end. This can lower the profile of the exit end 345, making it easier to advance in certain anatomies.

Further, the guide conduit 340 can be oriented so that it does not include an exit end that is angled laterally toward or away from the imaging portion 314. In this manner, a guide element 70 that is advanced along an axis 352 advances generally forward and outward, away from the blade 312 as shown. Such a construction can have an advancement axis that aligns with other axes and planes like that shown in FIG. 16. The guide conduit 340, of course, still can be curved or angled so that the guide element 70 diverges upward and away from the plane of the blade 312, generally aligned with the laryngeal axis, which is described above in connection with the current embodiment above. Of course, if diverging from the plane of the blade 312 is undesirable, the conduit 340 can be oriented differently.

IX. Seventh Alternative Embodiment

A seventh alternative embodiment of the laryngoscope guide is illustrated in FIG. 25 and generally designated 410. The laryngoscope guide 410 of this embodiment is similar in construction and operation to the above embodiments with several exceptions. For example, while the guide conduit 440 can include a major portion 441 and a minor portion 443 that are angled relative to one another at a junction 456, the exit end 445 of the guide conduit 440 can be modified. Specifically, it can be truncated at an angled portion 449 so that the guide bore 446 is bounded only along the portion of its periphery at the exit end 445. Generally, the end of the minor portion 443 can be cut or removed or otherwise truncated to provide a slightly greater field of view FOV for the imaging system 425 in the imaging portion 414. The precise angle at which the exit end 440 is cut or removed, and the amount of material around the periphery of the bore 446, can vary as desired. The slightly increased field of view FOV can enable a viewer to view the introducer 70 as it is fed along an advancement axis 452, out from the guide conduit 440 to align and steer it, as with the other embodiments herein.

X. Eighth Alternative Embodiment

An eighth alternative embodiment of the laryngoscope guide is illustrated in FIG. 26 and generally designated 510. The laryngoscope guide 510 of this embodiment is similar in construction and operation to the above embodiments with several exceptions. For example, the cylindrical tubular guide conduit 540 shown in the above embodiments can be replaced with a guide conduit 540 having a different geometry. As shown, the geometry can be of a generally square shape with the conduit 540 being defined by an adjoining wall 516, shared with the imaging portion 514, an upper wall 541, a sidewall 543 and a bottom, which can generally be a portion of the flange 517 and/or a portion of the blade 512. Although shown as a square, the geometric cross section of this guide conduit 540 can vary, for example, it can be triangular, parabolic, partially circular-like or any other geometric shape.

This construction can be formed via a molding operation in which portions of the mold are projected upward, into a cavity defined by the imaging portion 514, and later withdrawn, so that the imaging portion 514 is left with an internal bore (not shown). Likewise, the internal bore 546 of the guide conduit 540 can be similarly formed. Of course, the adjoining wall 516 can be formed between the pieces of the mold that are withdrawn from the respective bores of the imaging portion 514 and the guide conduit 540. Alternatively, the adjoining wall 516 can be absent altogether, with the guide bore 546 and the internal bore (not shown) of the imaging portion being continuous.

Optionally, the laryngoscope guide 510 can include an additional guide projection 566 that can assist in guiding the guide element 70 along an advancement axis 52. The guide projection 566 can be in the form of a cylindrical post or any other projection of any other geometric configuration. Alternatively, it may simply be a short tab or flange extending upwardly from the guide blade 512 at a predetermined distance from the exit end 545 of the guide conduit 540. The guide projection 566 can be placed at a variety of locations on the guide blade 512 depending on the intended trajectory of the flexible introducer 70 and the related advancement axis 552.

XI. Ninth Alternative Embodiment

A ninth alternative embodiment of the laryngoscope guide is illustrated in FIG. 27 and generally designated 610. The laryngoscope guide 610 of this embodiment is similar in construction and operation to the embodiments above with several exceptions. For example, the guide conduit 640 can be similar in configuration to that of the fifth alternative embodiment described immediately above. The guide conduit 640, however, can be modified slightly to include a deflection flange 644 that is integral with sidewall 643. The deflection flange 644 can engage the introducer 70 and direct it generally along the advancement axis 652. Although shown as a full height wall, the deflection flange 644 can be tapered or angled from top to bottom, with a smaller dimension as it nears the top of the blade. Optionally, the deflection flange 644 can also extend farther away from the guide conduit 640 toward the tip of the guide blade 612 as desired.

XII. Tenth Alternative Embodiment

A tenth alternative embodiment of the laryngoscope guide is illustrated in FIGS. 28-30 and generally designated 710. The laryngoscope guide 710 of this embodiment is similar in construction and operation to the embodiments above with several exceptions. For example, the guide conduit 740 can be constructed from an upper wall 741 and adjoining wall 716 that is shared between the imaging portion 714 and the guide conduit 740, and the blade flange 717. The walls can all be integrally formed together in a molding operation and can generally form a channel 722, for example, a c-shaped channel, defined by the upper wall 741, the adjoining wall 716 and the flange 717. The resulting channel can be closed by joining a separately formed wall 719 with the edges or other portions of a upper wall 741 and the flange 717 as shown by the direction of the arrow in FIG. 28. The separately formed wall 719 can be constructed from the same material as the remainder of the laryngoscope guide 710, or it can be constructed of a different material, such as polyvinylchloride, polyethylene, or some other polymer, metal or composite.

A perspective view of the separately constructed wall 719 is illustrated in FIG. 29. Generally, it follows the contours of the laryngoscope guide 710, and in particular, the contours corresponding to the guide conduit 740, and the respective channel formed by the walls thereof. The separate wall 719 can be joined with the edges or other portions of the upper wall 741 and the flange 717 with fasteners, glue, adhesive, a hot melt process, an ultrasonic welding process, a vibration melt process, radio frequency welding, laser melting or virtually any other process. Optionally, the joining of the separate wall can occur after the other components of the guide blade 710 are fully molded.

FIG. 30 also illustrates the completed guide conduit 740 with the wall 719 joined with the respective upper wall 741 and the flange 717 and/or a portion of the guide blade 712. The separate wall 719 can come in a variety of configurations. For example, it can be configured so that its end, adjacent the exit end 745 of the conduit 740 includes a deflection flange 744, much like that explained in the embodiments above. The deflection flange 744 can be configured in a variety of manners, and can deflect a corresponding guide element along a desired advancement axis.

XIII. Eleventh Alternative Embodiment

An eleventh alternative embodiment of the laryngoscope guide is illustrated in FIGS. 31-35 and generally designated 810. The laryngoscope guide 810 of this embodiment is similar in construction and operation to the embodiments above, and in particular, the seventh alternative embodiment, with several exceptions. For example, the guide conduit 840 can be at least partially constructed by a shared adjoining wall 816, an upper wall 841 and a lower wall 839. This configuration can generally form a c-shaped channel 822. Of course, the channel can be of other geometric configurations as desired.

The lower wall 839 is raised slightly above the flange 817. Collectively, the lower wall 839 and upper wall 841 can be slightly indented to form a recess 838 into which a guide conduit plate 819 (FIGS. 33-35) is received. The lower wall 839 can be raised a desired distance above the lower flange 817, depending on the particular configuration of the c-shaped channel and the resulting guide conduit 840. The interior of the c-shaped channel 822 can include various contours that assist in guiding a guide element through the finished guide conduit 840 along a desired advancement axis.

Figure 31:
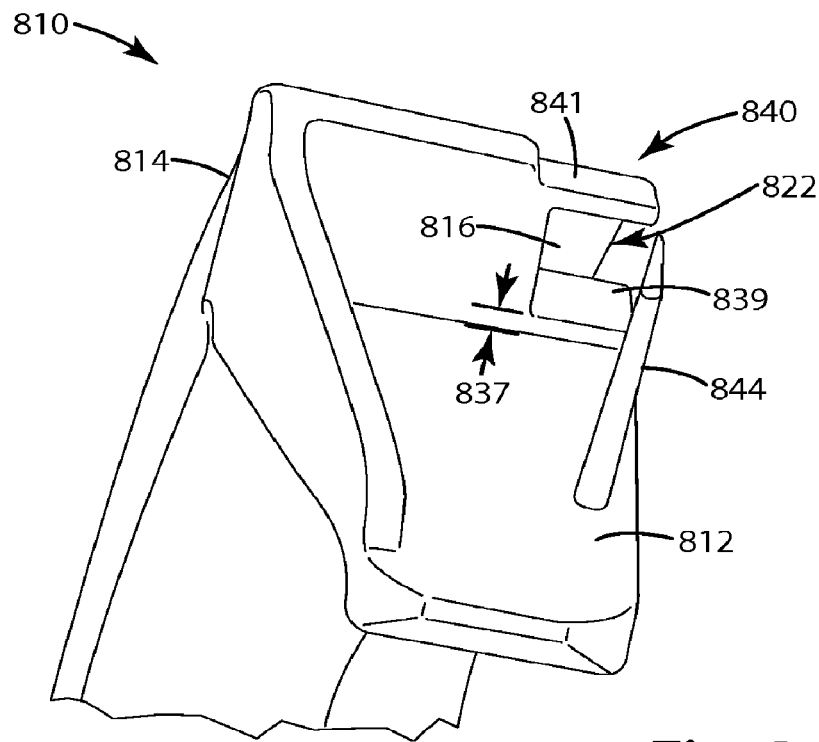
FIG. 31 is a front perspective view of an eleventh alternative embodiment of the laryngoscope guide, including a deflection flange without a guide conduit plate joined with the guide.
Figure 32:
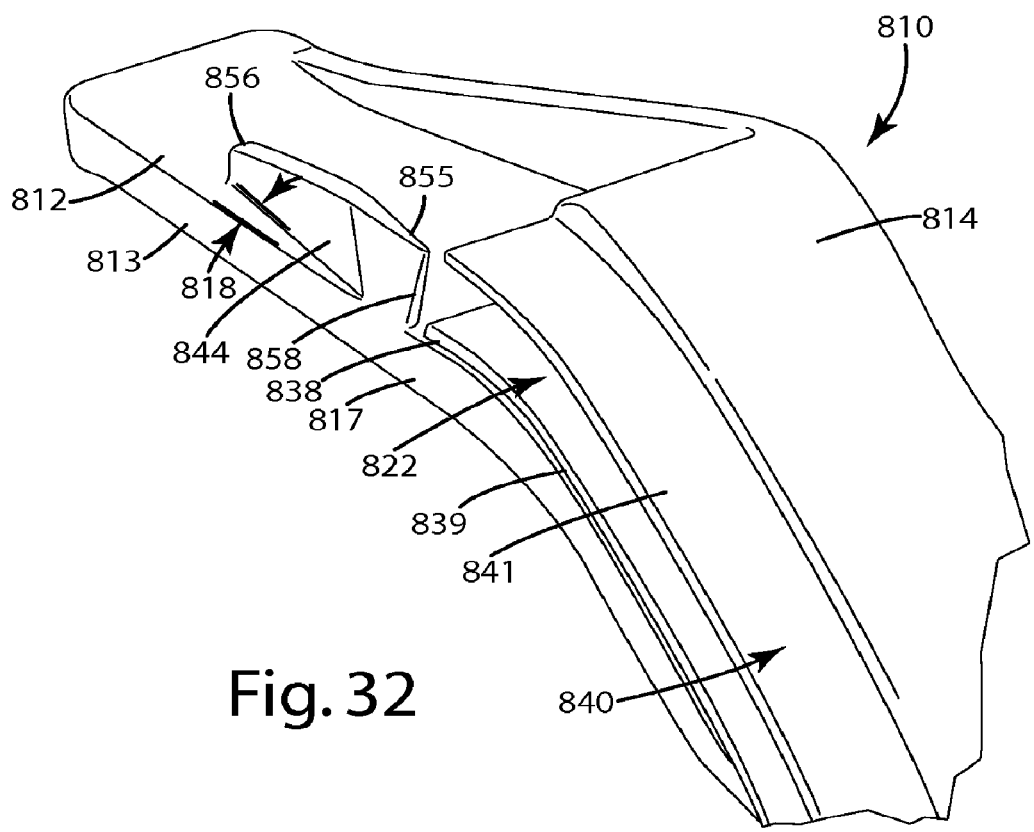
FIG. 32 is a rear perspective view of the eleventh alternative embodiment of the laryngoscope guide, including a deflection flange, without a guide conduit plate joined with the guide.

As shown in FIGS. 31 and 32, lower wall 839 can be raised a distance 837 above the laryngoscope guide blade 812. This distance can be selected to provide the guide element, when placed to the guide conduit 840, a desired trajectory diverging from the guide blade 812. This distance 837 can be 0.1 mm to about 3 mm to about 4 mm, or other increments therebetween, depending on the application. Further, the angle between the blade and the conduit can be any of the angles described in connection with the current embodiment above to provide the desired amount of divergence of the introducer from the blade after the introducer leaves the conduit along an advancement axis.

Referring to FIGS. 31 and 32, the laryngoscope guide 810 also can include a deflection flange 844 that is integral with the laryngoscope guide blade 812. The deflection flange 844 can be offset at an angle 818 relative to the outside periphery or edge 813 of the laryngoscope guide blade 812. This angle can range from about 1° to about 15°, optionally about 25° to about 30°. Optionally, the deflection flange can be configured so that its end can deflect the corresponding guide element along a desired advancement axis as with the embodiments described above.

The rearward portion of the deflection flange 844 can be integrally molded with the blade 812 and can reduce in height as it extends from the rearward portion 855 to the forward portion 856. The rearward portion 855 can also include a guide conduit plate engaging surface 858 to which the guide conduit plate 818 can be joined by any desired method, for example, via ultrasonic welding, radio frequency welding, laser welding or any of the aforementioned techniques for joining one part to another described in the embodiments above. Further, this guide conduit plate joining surface 858 can also form a portion of the recess 838 into which the guide conduit plate 818 fits and is joined.

Figure 33:
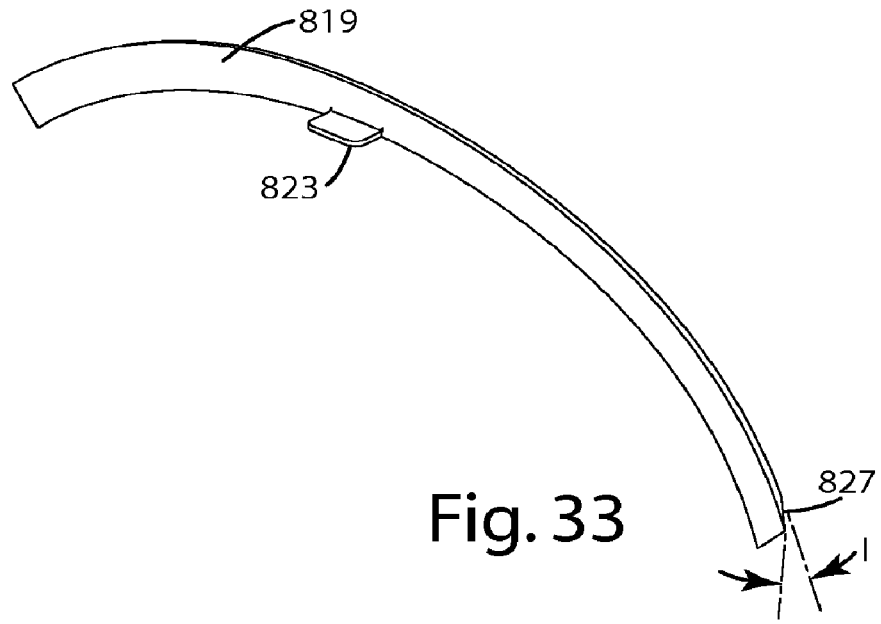
FIG. 33 is a side view of a guide conduit plate of the eleventh alternative embodiment of the laryngoscope guide.

Referring to FIG. 33, the guide conduit plate 819 can include a forward portion 827 that is angled at an angle I, which can vary depending on how the guide conduit plate, also referred to as a side plate or guide plate 819, transitions to the deflection flange 844. As illustrated, the end 827 can be angled relative to the remainder of the plate at an angle I of about 0.5° to about 3° or about 5°. Other angles may be selected as desired. The side plate 819 can also include a tab 823 that is positioned adjacent the connector tab 825 when installed on the guide 810. This tab 823 can be generally orthogonal or at a right angle relative to the remainder of the side plate 819. The tab 823 can provide certain alignment of the guide plate relative to the c-shaped channel 822 and can assist in holding the guide plate in a predetermined orientation before it is welded or otherwise joined to the remaining portion of the guide conduit 840.

Figure 34:
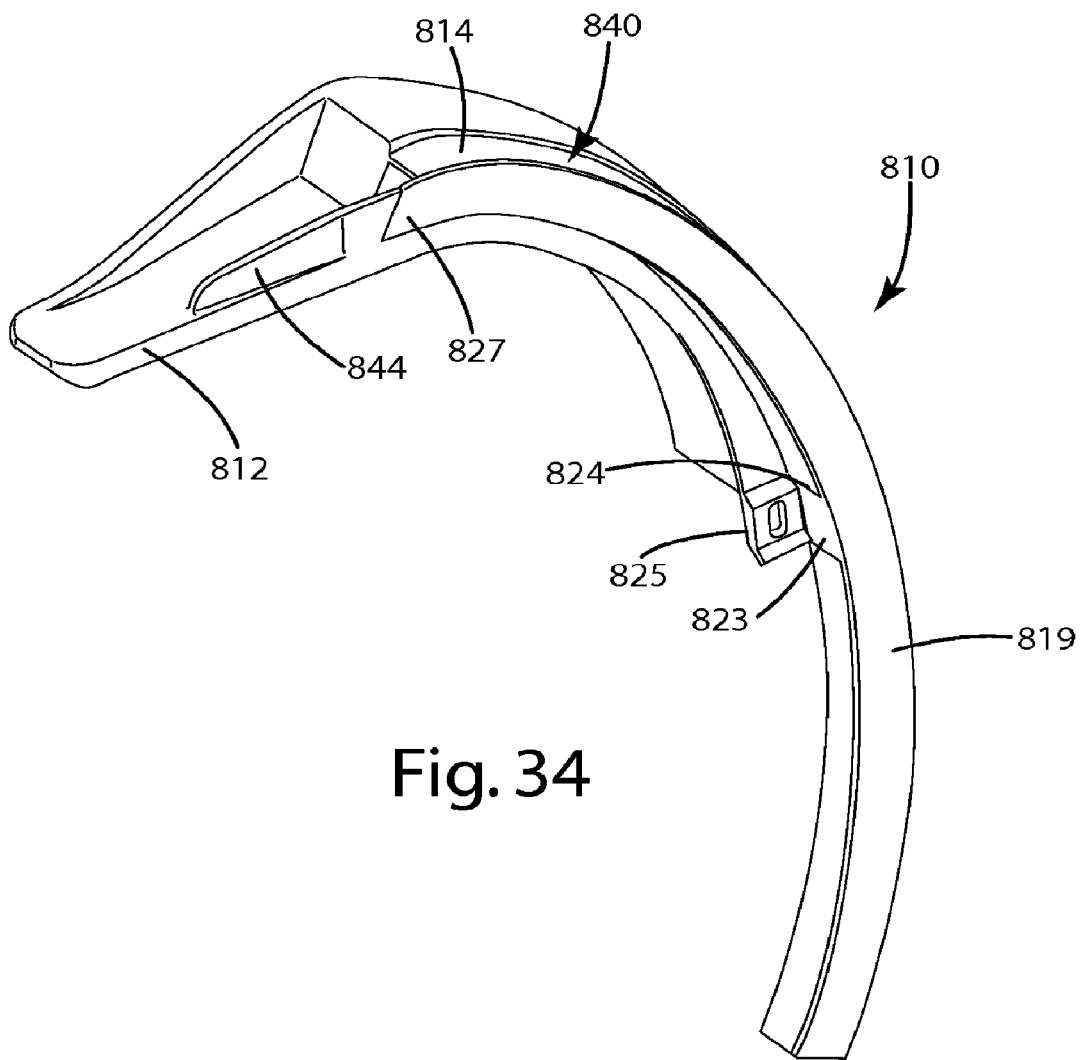
FIG. 34 is a side perspective view of the eleventh alternative embodiment of the laryngoscope guide with the guide conduit plate joined with the guide.
Figure 35:
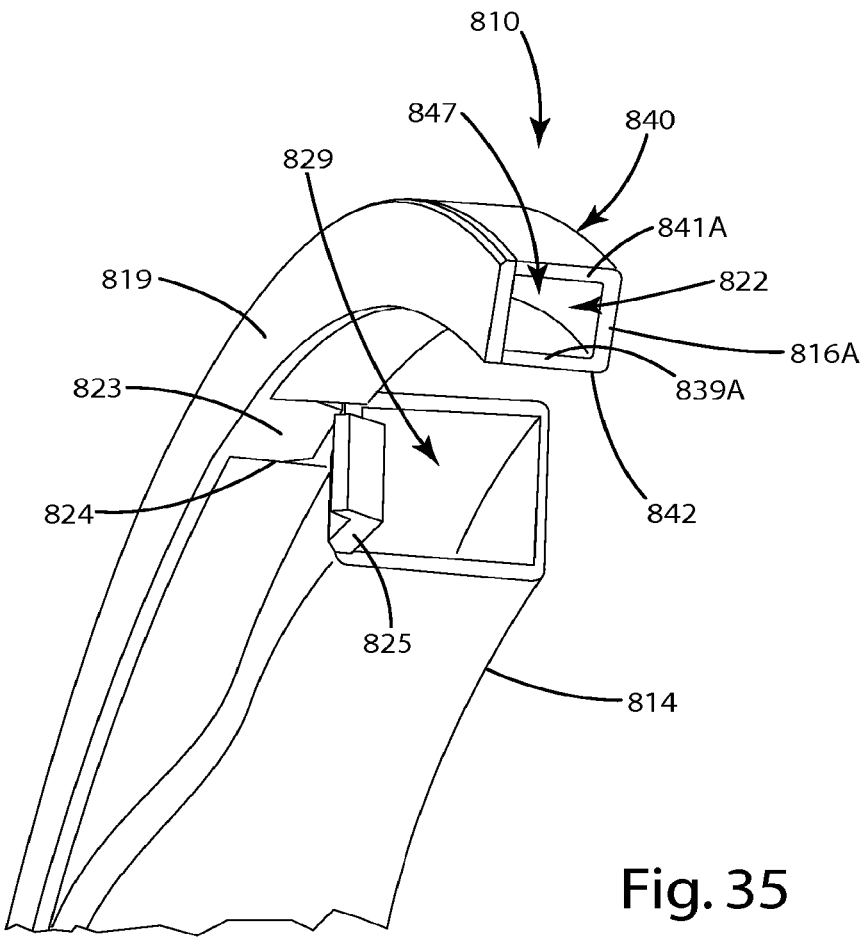
FIG. 35 is a rear perspective view of the eleventh alternative embodiment of the laryngoscope guide with the guide conduit plate joined with the guide.

As shown in FIGS. 34 and 35, the guide tab 823 can interfit within the guide tab recess 824 defined by the lower wall 839 of the guide conduit 840. The guide plate 819 generally can close off the c-shaped channel 822 as shown there. The walls that define the c-shaped channel 822, namely, 841, 816 and 839 can transition to the walls 841A, 816A and 839A in the rearward portion of the guide conduit 840 in transitioning to the exit end 847 of the guide conduit 840. As further shown in FIG. 35, the channel 822 formed by walls 841A, 816A and 839A can be closed off with the side plate 819, joined with those walls. As also shown in FIGS. 34 and 35, the guide conduit 840 can extend a predetermined distance beyond the end 829 of the imaging portion 814, depending on how far away from the laryngoscope guide blade the professional desires the exit 847 to be located to properly insert a guide element in use.

As with the embodiments noted above, the components of the guide blade 810 can be integrally molded, for example, through plastic injection molding. The channel 822 can be formed in this process. Optionally, the guide conduit plate 819 with its components can also be separately formed of the same or of a different material. In one example, the laryngoscope guide 810 can be constructed from a first material, such as a polymer, like a dense but clear plastic, and the guide plate 819 can be constructed from a second material, such as polyvinylchloride or some other suitable material.

With the guide blade 810 and the guide plate 819 formed, the guide plate 819 can be interfitted within the recess 838 formed by the various components of the laryngoscope guide 810. The tab 823 of the guide conduit plate 819 can also be interfitted in the corresponding recess 824 in the lower wall 839a of the guide conduit 840. The components of the guide plate 819 can then be permanently joined with the corresponding components of the laryngoscope guide 810, for example, by ultrasonic welding, laser welding, fasteners, glue, adhesive, hot-melt process, vibration-melt process or virtually any other process described herein. After the parts are joined, they can be finished and packaged as desired.

XIV. Twelfth Alternative Embodiment

Figures 36, 37:
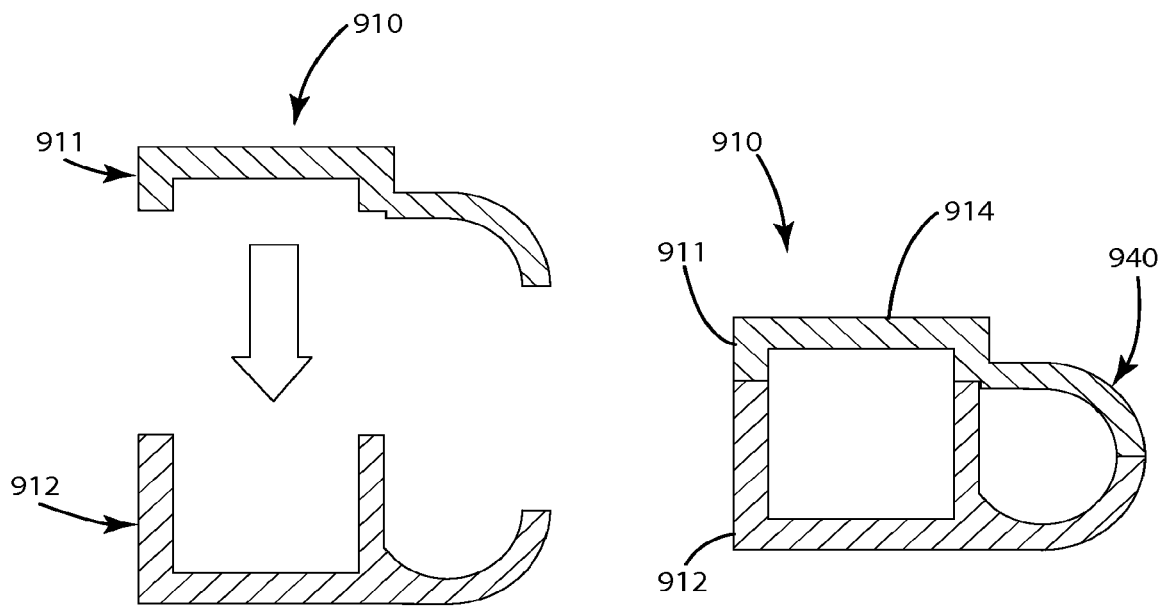
FIG. 36 is an unassembled section view of a twelfth alternative embodiment of the laryngoscope guide.
FIG. 37 is an assembled section view of the twelfth alternative embodiment of the laryngoscope guide.

A twelfth alternative embodiment of the laryngoscope guide is illustrated in FIGS. 36-37 and generally designated 910. The laryngoscope guide 910 of this embodiment is similar in construction and operation to the embodiments above, with several exceptions. For example, the laryngoscope guide 910 can be constructed from opposing first 911 and second 912 portions. These portions can at least partially define the imaging portion 914 configured to accept at least a portion of an imaging system of a laryngoscope and the guide conduit 940.

As shown in FIG. 37, the first portion 911 can define the upper portion of the imaging portion and the guide conduit, while the second portion 912 can form the lower portion of the imaging portion 914 and the lower portion of the guide conduit 940. Although shown as bisecting the section of the laryngoscope guide along a horizontal plane, the first and second portions can be divided along different planes or axes of the laryngoscope guide 910 as desired. Optionally, the laryngoscope guide 910 also can be divided into additional portions.

To construct the laryngoscope guide, the first portion 911 and second portion 912 can be joined together at an interface as shown in FIG. 37 using a variety of methods. For example, the first portion 911 and second portion 912 can be joined by a holt melt process, ultrasonic welding, laser welding, a vibration melt process, fasteners, glue, adhesives or any other processes described herein. After the first and second portions are joined to form the laryngoscope guide 910, the guide can be finished and packaged.

The above descriptions are those of the preferred embodiments of the invention. Various alterations and changes can be made without departing from the spirit and broader aspects of the invention as defined in the appended claims, which are to be interpreted in accordance with the principles of patent law including the doctrine of equivalents. Any references to claim elements in the singular, for example, using the articles "a," "an," "the," or "said," is not to be construed as limiting the element to the singular. Any reference to claim elements as "at least one of X, Y and Z" is meant to include any one of X, Y or Z individually, and any combination of X, Y and Z, for example, X, Y, Z; X, Y; X, Z; and Y, Z.

The invention claimed is:

1. A method of intubating a subject, the method comprising:
providing a portable, hand held laryngoscope including a handle and an imaging system adapted to communicate image data to a monitor, the imaging system having a field of view within which an optical axis projects, and a laryngoscope guide joined with the handle, the laryngoscope guide including a blade having a distal tip and a laryngoscope guide element in the form of a conduit, the conduit terminating at an exit proximal to the distal tip, the conduit defining an advancement axis that projects into the field of view, the advancement axis disposed at a first angle relative to the optical axis and oriented to traverse the optical axis;
positioning the laryngoscope guide in an airway of the subject;
engaging the blade against tissue in the airway with a force sufficient to move the tissue and establish a viewing volume so that the airway is within the field of view of the imaging system;
sliding a flexible introducer, including a primary portion and a distal end, at least partially through the conduit with the flexible introducer bending to conform to internal contours of the conduit as the flexible introducer slides in the conduit, and with the flexible introducer extending beyond the exit and entering the field of view of the imaging system;
advancing the flexible introducer along the advancement axis so that the conduit establishes at least a portion of the trajectory of the flexible introducer, and so that the flexible introducer travels toward the optical axis;
observing the image data communicated to the monitor to align the distal end of the flexible introducer with an opening to the trachea of the subject displayed on the monitor;
continuing to advance the flexible introducer along the advancement axis so that the distal end enters the opening to the trachea forward of the blade;
removing the laryngoscope guide from the airway, with the distal end of the flexible introducer remaining in the opening to the trachea, and with the primary portion and conduit sliding relative to one another until the laryngoscope guide and laryngoscope are separated from the flexible introducer, and completely removed from the airway;
installing a tube relative to the primary portion of flexible introducer after the laryngoscope guide is removed from the airway so that the tube is coaxially oriented relative to the primary portion of the flexible introducer;
guiding the tube coaxially along the primary portion of the flexible introducer toward the distal end after said tube installing step so that a tube end of the tube enters the opening to the trachea adjacent the distal end of the flexible introducer; and
removing the flexible introducer from the tube while leaving the tube end in the opening to the trachea to establish fluid communication between the trachea and a location outside the airway with the tube.

2. The method of claim 1 comprising advancing the flexible introducer along the advancement axis so that it intersects a first blade plane that is perpendicular to and bisects at least one of the blade and the distal tip of the laryngoscope guide.

3. The method of claim 2 wherein the blade includes a superior portion forward of the imaging system, wherein the superior portion defines a second blade plane that is perpendicular to the first blade plane, wherein the flexible introducer diverges at a second angle away from the second blade plane as the flexible introducer is advanced along the advancement axis.

4. The method of claim 3 wherein the second angle is preselected so that the advancement axis is aligned with a laryngeal axis of the subject while the blade is engaged against the tissue in the airway.

5. The method of claim 1 comprising wherein the blade of the laryngoscope guide completely disengages and is completely removed from the subject during said removing of the laryngoscope guide from the airway.

6. The method of claim 1 wherein the conduit includes a major portion and a minor portion, the minor portion disposed at a third angle relative to the major portion, wherein as the flexible introducer is advanced from the major portion to the minor portion, the conduit imparts a bending force on the flexible introducer.

7. The method of claim 1 wherein said positioning the laryngoscope guide in the airway is performed while the subject's head is in a neutral position, with an oral axis of the subject misaligned with both of a pharyngeal axis and a laryngeal axis of the subject.

8. A method of intubating a subject comprising:
providing a portable, hand held laryngoscope including a handle, a monitor joined with and moveable with the handle, and a guide attachment end, the guide attachment end including an imaging system and a light source, the imaging system adapted to communicate image data to the monitor, the imaging system having a field of view within which an optical axis projects;
providing a disposable laryngoscope guide including a laryngoscope attachment end that is adapted to removably join the laryngoscope guide and the laryngoscope, the laryngoscope guide including a blade having a superior portion and an inferior portion opposite the superior portion, the superior portion and inferior portion joining at a distal tip of the blade, the blade defining a lateral portion and a medial portion with a first blade plane being generally vertical relative to the superior portion and being defined midway between the lateral portion and the medial portion, the laryngoscope guide including a viewing window adjacent the superior portion, the laryngoscope guide including a laryngoscope guide element in the form of a conduit extending from the laryngoscope attachment end toward the field of view, the conduit terminating at an exit and defining an advancement axis, the advancement axis projecting outwardly from the exit and intersecting the first blade plane forward of the viewing window;
joining the disposable laryngoscope guide with the portable, hand held laryngoscope at the guide attachment end, with the imaging system positioned so the optical axis projects through the viewing window and the field of view encompasses an area forward of the viewing window;
positioning the laryngoscope guide in an oral cavity of the subject;
advancing the blade toward the glottis of the subject;
engaging at least one of the superior portion and the inferior portion of the blade against tissue with a force sufficient to move the tissue and establish a viewing volume, the glottis being within the field of view, with image data concerning the glottis being communicated to the monitor;
advancing a flexible introducer, including a distal end and a primary portion, in the laryngoscope guide element so that the flexible introducer flexibly conforms to internal contours of and follows the conduit until the distal end exits the conduit at the exit end of the conduit;
continuing to advance the flexible introducer along at least a portion of the advancement axis so that the flexible introducer enters the field of view of the imaging system;
observing the image data communicated to the monitor to determine the position of the distal end relative to the glottis on the monitor;
aligning the flexible introducer distal end with the glottis;
continuing to advance the flexible introducer so that the flexible introducer intersects the first blade plane and so that the distal end of the flexible introducer enters the glottis;
removing the laryngoscope guide from the subject and from the flexible introducer, with the distal end of the flexible introducer remaining in the glottis, and the primary portion and conduit sliding coaxially relative to one another until the laryngoscope guide is removed from the flexible introducer so that the distal end of the flexible introducer no longer in the field of view of the imaging system;
positioning an endotracheal tube in a coaxial arrangement relative to the primary portion of the flexible introducer after said removing the laryngoscope guide step;
guiding the endotracheal tube along the primary portion of the flexible introducer toward the distal end so that a tube end of the endotracheal tube enters the glottis of the subject; and
removing the flexible introducer from the glottis while leaving the endotracheal tube in position with the tube end in the glottis of the subject.

9. The method of claim 8 wherein the advancement axis diverges at an angle away from the superior portion of the blade so that as the flexible introducer is advanced, the flexible introducer diverges at the angle away from the superior portion of the blade.

10. The method of claim 8 wherein said positioning the laryngoscope guide in the oral cavity of the subject is performed while the subject's head is in a neutral position, with an oral axis of the subject misaligned with both of a pharyngeal axis and a laryngeal axis of the subject.

11. The method of claim 8 wherein the flexible introducer advances along at least a portion of the advancement axis so that the flexible introducer enters the field of view of the imaging system from a lateral portion of the field of view and continues to advance above the superior portion of the blade.

12. The method of claim 8 wherein the conduit is at least partially arc-shaped, wherein the flexible introducer slides through the conduit as the flexible introducer advances therein, wherein the flexible introducer reconfigures from a generally linear configuration to the arc-shape of the conduit as the flexible introducer slides in the conduit.

13. The method of claim 8 wherein the step of continuing to advance the flexible introducer so that the flexible introducer intersects the first blade plane includes advancing the flexible introducer at a first angle between 1° to 25° relative to the first blade plane.

14. The method of claim 8 wherein the step of continuing to advance the flexible introducer so that the flexible introducer intersects the first blade plane includes advancing the flexible introducer so that it intersects the first blade plane forward of the distal tip of the blade.

15. The method of claim 8 wherein the blade defines a second blade plane being generally horizontal and extending between the lateral portion and medial portion of the blade, wherein the conduit is positioned so that the exit is located a preselected distance above the second blade plane, wherein the advancement axis is oriented so as to diverge away from the second blade plane.

16. The method of claim 15 wherein the step of continuing to advance the flexible introducer along at least a portion of the advancement axis so that the flexible introducer enters the field of view of the imaging system includes advancing the flexible introducer so that it diverges away from the second blade plane and aligns with a laryngeal axis of the subject.

17. A method for intubating a subject comprising:
placing a laryngoscope guide in an airway, the laryngoscope guide at least partially housing an imaging system having a field of view and an optical axis, the laryngoscope guide including a blade having a distal tip and a first blade plane that generally bisects at least one of the distal tip and the blade, the laryngoscope guide including a conduit;

engaging the blade against tissue in the airway with a force sufficient to move the tissue and establish a viewing volume, a glottis of the subject being within the field of view of the imaging system;

sliding a flexible introducer, including a primary portion, and a distal end, at least partially through the conduit with the flexible introducer conforming to internal contours of the conduit as the flexible introducer and conduit slides relative to one another;

advancing the flexible introducer toward the first blade plane at a first angle so that the flexible introducer projects along an advancement axis aligned to traverse at least one of the first blade plane and the optical axis so that the flexible introducer enters the field of view of the imaging system and advances over a superior portion of the blade;

placing the distal end of the flexible introducer in the glottis;

removing the laryngoscope guide from the airway and from the flexible introducer, with the distal end of the flexible introducer remaining in the glottis, with the blade becoming disengaged from the tissue during said removing step, and with the flexible introducer becoming separated from the laryngoscope guide during said removing step;

guiding an endotracheal tube along the flexible introducer toward the distal end, after said laryngoscope guide removing step, so that a tube end of the endotracheal tube enters the glottis of the subject; and removing the flexible introducer while leaving the tube end in the glottis whereby the subject is intubated.

18. The method of claim 17 wherein the advancement axis diverges at a second angle away from the superior portion of the blade so that as the flexible introducer is advanced, the flexible introducer diverges at the second angle away from the superior portion of the blade.

19. The method of claim 18 wherein the first angle is between 1° and 25° and wherein the second angle is between 1° and 35°.

20. The method of claim 18 wherein the conduit slides coaxially relative to the flexible introducer, and wherein the blade is completely removed from the airway and the subject during the removing the laryngoscope guide step.

* * * * *